United States Patent [19]

Waterhouse et al.

[11] Patent Number: 6,005,663
[45] Date of Patent: *Dec. 21, 1999

[54] AUTOMATED ELECTROPHORESIS AND FLUORESCENCE DETECTION APPARATUS AND METHOD

[75] Inventors: Paul Waterhouse, Copetown; John A. Renfrew, Burlington; John K. Stevens, Toronto, all of Canada

[73] Assignee: Visible Genetics Inc., Toronto, Canada

[*] Notice: This patent is subject to a terminal disclaimer.

[21] Appl. No.: 08/849,662

[22] PCT Filed: Dec. 12, 1995

[86] PCT No.: PCT/US95/15951

§ 371 Date: Aug. 18, 1997

§ 102(e) Date: Aug. 18, 1997

[87] PCT Pub. No.: WO96/18892

PCT Pub. Date: Jun. 20, 1996

Related U.S. Application Data

[63] Continuation-in-part of application No. 08/353,932, Dec. 12, 1994, Pat. No. 5,710,628.

[51] Int. Cl.[6] .................................................. G01N 21/00
[52] U.S. Cl. ......................... 356/344; 204/461; 204/466; 204/612
[58] Field of Search ................................... 356/344, 445, 356/446, 447, 448

[56] References Cited

U.S. PATENT DOCUMENTS

| | | | |
|---|---|---|---|
| 3,916,197 | 10/1975 | Fulwyler | 356/335 |
| 4,329,591 | 5/1982 | Fujiwara et al. | 250/548 |

(List continued on next page.)

FOREIGN PATENT DOCUMENTS

| | | |
|---|---|---|
| 0157280 | 10/1985 | European Pat. Off. . |
| 454286 | 10/1991 | European Pat. Off. . |

(List continued on next page.)

OTHER PUBLICATIONS

Smith et al., "Sequence Detection in Automated DNA Analysis," *Nature* 321: 674–679 (1986).
Hjerten, S., "Free zone electrophoresis" in *Chromatographic Reviews* 9: 122–219 (1967).

Primary Examiner—Frank G. Font
Assistant Examiner—Roy M. Punnoose
Attorney, Agent, or Firm—Oppedahl & Larson LLP

[57] ABSTRACT

Improved detection methods and apparatus which may be used individually or in combinations enhance the ability of the electrophoresis apparatus to detect fluorophore-labeled materials in short periods of time. One such apparatus comprises a housing adapted to receive an electrophoresis gel holder; an excitation source of electromagnetic radiation having a frequency effective to induce emission of electromagnetic radiation from the fluorophore; a plurality of optical fibers for delivering electromagnetic radiation from the excitation source to a linear array of excitation/detection sites on the gel holder, optical switching means for sequentially directing electromagnetic radiation into one of several pre-defined groups of the optical fibers; detection means such as a photomultiplier tube, or an array of photomultiplier tubes for detecting emission from the fluorophore induced by a radiation from the excitation source; and means for correlating a detected emission with the switching of the excitation electromagnetic radiation such that a given emission may be linked with the excitation/detection site being irradiated. For example, the optical switching means may alternate between directing radiation from the source into every other optical fiber, or may provide radiation in rotation to every third or fourth fiber. Alternatively, a spot array generation grating can be used for dividing an incident beam of coherent radiation into an array of excitation beamlets and directing each excitation beamlets to an excitation/detection site on the electrophoresis gel. Light emitting diode disposed to deliver excitation energy to an array of excitation/detection sites may also be used. This latter form of the apparatus is particularly advantageous due to the low costs of light emitting diodes (LEDs) compared to coherent light sources (e.g. lasers).

40 Claims, 15 Drawing Sheets

U.S. PATENT DOCUMENTS

| | | | |
|---|---|---|---|
| 4,343,991 | 8/1982 | Fujiwara et al. | 250/227 |
| 4,811,218 | 3/1989 | Hunkapiller | 364/413.01 |
| 4,823,007 | 4/1989 | Hanson | 250/327.2 |
| 4,832,815 | 5/1989 | Kambara et al. | 204/299 R |
| 4,881,812 | 11/1989 | Ohkubo et al. | 356/344 |
| 4,927,265 | 5/1990 | Brownlee | 356/73 |
| 4,930,893 | 6/1990 | Manian | 356/344 |
| 4,960,999 | 10/1990 | McKean et al. | 250/461.1 |
| 4,981,977 | 1/1991 | Southwick et al. | 548/455 |
| 5,006,210 | 4/1991 | Yeung et al. | 204/180.1 |
| 5,045,172 | 9/1991 | Guzman | 204/299 R |
| 5,051,162 | 9/1991 | Kambara et al. | 204/299 R |
| 5,062,942 | 11/1991 | Kambara et al. | 204/299 R |
| 5,069,769 | 12/1991 | Fujimiya et al. | 204/182.8 |
| 5,091,652 | 2/1992 | Mathies et al. | 250/458.1 |
| 5,100,529 | 3/1992 | Fuji | 204/299 R |
| 5,108,179 | 4/1992 | Myers | 356/344 |
| 5,119,316 | 6/1992 | Dam et al. | 364/498 |
| 5,122,345 | 6/1992 | Tabor et al. | 422/116 |
| 5,162,654 | 11/1992 | Kostichka et al. | 250/458.1 |
| 5,171,534 | 12/1992 | Smith et al. | 422/82.05 |
| 5,190,632 | 3/1993 | Fujiyama et al. | 204/299 R |
| 5,207,880 | 5/1993 | Middendorf | 204/182.2 |
| 5,208,466 | 5/1993 | Pentoney, Jr. | 250/574 |
| 5,213,673 | 5/1993 | Fujiyama et al. | 204/299 R |
| 5,230,781 | 7/1993 | Middendorf et al. | 204/182.2 |
| 5,242,567 | 9/1993 | Fujiyama et al. | 204/299 R |
| 5,246,866 | 9/1993 | Nasu et al. | 436/94 |
| 5,268,486 | 12/1993 | Waggoner et al. | 548/427 |
| 5,274,240 | 12/1993 | Mathies | 250/458.1 |
| 5,290,419 | 3/1994 | Kambara et al. | 204/299 R |
| 5,294,323 | 3/1994 | Togusari et al. | 204/299 R |
| 5,307,148 | 4/1994 | Kambara et al. | 356/344 |
| 5,314,602 | 5/1994 | Kambara et al. | 204/299 R |
| 5,324,401 | 6/1994 | Yeung et al. | 204/180.1 |
| 5,360,523 | 11/1994 | Middendorf et al. | 204/182.2 |
| 5,365,455 | 11/1994 | Tibbetts et al. | 364/497 |
| 5,410,412 | 4/1995 | Gombocz et al. | 356/417 |
| 5,419,825 | 5/1995 | Fujii | 204/299 |
| 5,420,691 | 5/1995 | Kawaguchi | 356/375 |
| 5,439,578 | 8/1995 | Dovichi et al. | 356/344 |
| 5,534,125 | 7/1996 | Middendorf et al. | 204/612 |
| 5,710,628 | 1/1998 | Waterhouse et al. | 356/344 |

FOREIGN PATENT DOCUMENTS

| | | |
|---|---|---|
| 0483460 | 6/1992 | European Pat. Off. . |
| 0592060 | 4/1994 | European Pat. Off. . |
| 2411361 | 9/1975 | Germany . |
| 8707719 | 11/1987 | WIPO . |
| WO 9219975 | 12/1992 | WIPO . |
| 94/03631 | 2/1994 | WIPO . |

APERTURE SIZE 1-3mm

AUTOMATED ELECTROPHORESIS AND FLUORESCENCE DETECTION APPARATUS AND METHOD

This application is a continuation-in-part of U.S. patent application Ser. No. 08/353,932 filed Dec. 12, 1994, now U.S. Pat. No. 5,710,628 issued Jan. 20, 1998.

I. BACKGROUND OF THE INVENTION

This application relates to a method and apparatus for rapid gel electrophoresis and fluorescence detection of a complex mixture of fluorophore labeled proteins or nucleic acids.

Polyacrylamide gel electrophoresis (PAGE) separation of organic molecules is now routinely performed. *Current Protocols in Molecular Biology*, Chap. 10, John Wiley & Sons (1994). A polyacrylamide gel provides a suitably insoluble sieve so as to permit the separation of organic molecules in solution by size and conformation as they are drawn through the sieve under electromotive force. Such separation of organic molecules provides valuable insights into their structures and functions. For example, PAGE separation can separate two polypeptides of the same size but of different isoforms or polypeptides only 100 daltons different in size (Current Protocols, 1994). Another use for PAGE is in separation of nucleic acids based on size of fragments, such as in the extremely important application of DNA sequence determination. Maniatis, *Molecular Cloning, A Laboratory Manual*, 2nd ed., 1987.

Early methods for detection of separated products on an electrophoresis gel were carried out after the separation was completed. To the extent these techniques were automated in an apparatus, the apparatus generally including a mechanism for moving the gel in stages relative to a detector. For example, U.S. Pat. No. 4,343,991 discloses a sample detection apparatus in which stained bands within a gel are detected by transporting the gel between an array of optical fibers supplying incident light and an array of optical fibers collecting transmitted light. Information was collected in steps along the whole length of the gel. Devices of this type have the advantage that long sample collection times can be used when necessary to ensure detection of low intensity bands in the gel. However, they also have several drawbacks. In particular, because the gel is analyzed only after separation is completed, the degree of separation is necessarily a compromise between the desire to observe fast migrating bands (which run off the end of the gel if the electrophoresis proceeds too long) and the desire to separate slow moving band (which are still grouped together if the electrophoresis run is too short). In addition, the use of distinct separation and detection processes significantly lengthened the time required to complete an analysis. Thus, the art has generally sought the ability to detect bands on an electrophoresis gel during the separation.

When the electrophoresed molecules are labeled with a detectable signal, it is possible to detect the separations of molecules in real time. Since the first description of a real-time nucleic acid separation method and apparatus by Smith et al., Sequence Detection in Automated DNA Sequence Analysis", *Nature* 321:674–679 (1986), the technology for so-called automated DNA sequencing has expanded rapidly. Several automated DNA sequencing apparatuses are commercially available. Methods and apparatus for sequencing of DNA are described in U.S. Pat. Nos. 4,811,218; 4,881,812; 5,062,942; 5,091,652; 5,108,179; 5,122,345; 5,162,654; 5,171,534; 5,190,632; 5,207,880; 5,213,673; 5,230,781; 5,242,567; 5,290,419; 5,294,323; 5,307,148; 5,314,602; 5,324,401; and 5,360,523 which are incorporated herein by reference.

Unfortunately, the existing apparatuses are inadequate for use of PAGE for emerging clinical diagnostic purposes such as diagnostic DNA sequence and fragment analysis. For clinical diagnostic DNA analysis, it is desirable to examine hundreds of complex DNA samples per day. Existing technology does not provide for such capacity. For example, operation of a typical automated DNA sequencer to evaluate at most about 10 samples requires that a skilled technician spend up to four hours constructing a gel holder, filling the gel holder with actively polymerizing acrylamide solution, inserting a well-forming comb before substantial polymerization has occurred, and waiting for the gel to polymerize (see Maniatis, 1987). Using the gel is equally time consuming. Existing technologies use low density electric fields (less than 100 volts/cm) requiring sample running times of up to four hours. It would be advantageous to have an improved apparatus with improved sample throughput for real-time DNA analysis particularly for use in clinical diagnostic applications.

It is an object of this invention to provide a gel electrophoresis and fluorescence detection apparatus suitable for high throughput clinical diagnostic DNA and protein analysis.

It is a further object of the present invention to provide an electrophoresis apparatus which is capable of using gels which use a high magnitude electric field of 100–400 v/cm.

It is a further object of the invention to provide improved optical excitation and detection techniques for real time detection of fluorescently labeled DNA or protein samples in an electrophoresis gel.

II. SUMMARY OF THE INVENTION

The present invention achieves these and other objects by providing improved detection methods and apparatus which may be used individually or in various combinations to enhance the ability of the electrophoresis apparatus to detect fluorophore-labeled materials in short periods of time. Thus, one embodiment of the present invention is an apparatus for electrophoretic separation and real-time detection of a sample labeled with a fluorophore comprising:

(a) a housing adapted to receive an electrophoresis gel holder;

(b) an excitation source, of electromagnetic radiation;

(c) means for sequentially delivering electromagnetic radiation from the excitation source to each of a plurality of pre-defined excitation/detection sites within a linear array of excitation/detection sites on a gel holder disposed within the housing;

(d) means for applying an electric field for to a gel holder disposed within the housing for separation of a sample applied to a gel within the holder, and (e) means for detecting emissions from the sample at the excitation/detection site, wherein the housing holds the gel holder in a fixed position relative to the means for sequentially delivering electromagnetic radiation and the means for detecting emissions when the gel holder is disposed within the housing.

The electromagnetic radiation can be delivered to the excitation/detection sites using a plurality optical fibers or a spot array generation grating. In addition, the apparatus may advantageously include optical switching means for sequentially directing electromagnetic radiation into one of several pre-defined groups, each group including two or more of the excitation/detection sites, and means for correlating a detected emission with the switching of the excitation electromagnetic radiation such that a given emission may be linked with the excitation/detection site being irradiated. For example, when optical fibers are used to deliver the excitation electromagnetic radiation, the optical switching means may alternate between directing radiation from the source into every other optical fiber, or may provide radiation in rotation to every third or fourth fiber.

A alternative embodiment of the invention is an apparatus comprising (a) a housing adapted to receive an electrophoresis gel holder;

(b) at least one light emitting diode disposed to deliver excitation energy of a frequency suitable for excitation of the fluorophore to an array of excitation/detection sites on the gel holder, and (c) a detector, for example a photodiode, for detecting emissions from the array of excitation/detection sites. This latter form of the apparatus is particularly advantageous due to the low costs of light emitting diodes (LEDs) compared to coherent light sources (e.g. lasers).

III. BRIEF DESCRIPTION OF THE DRAWINGS

IV. DETAILED DESCRIPTION OF THE INVENTION

This application discloses a method and apparatus for rapid gel electrophoresis and real-time fluorescence detection of a complex mixture of fluorophore-labeled organic molecules.

Figure 1:
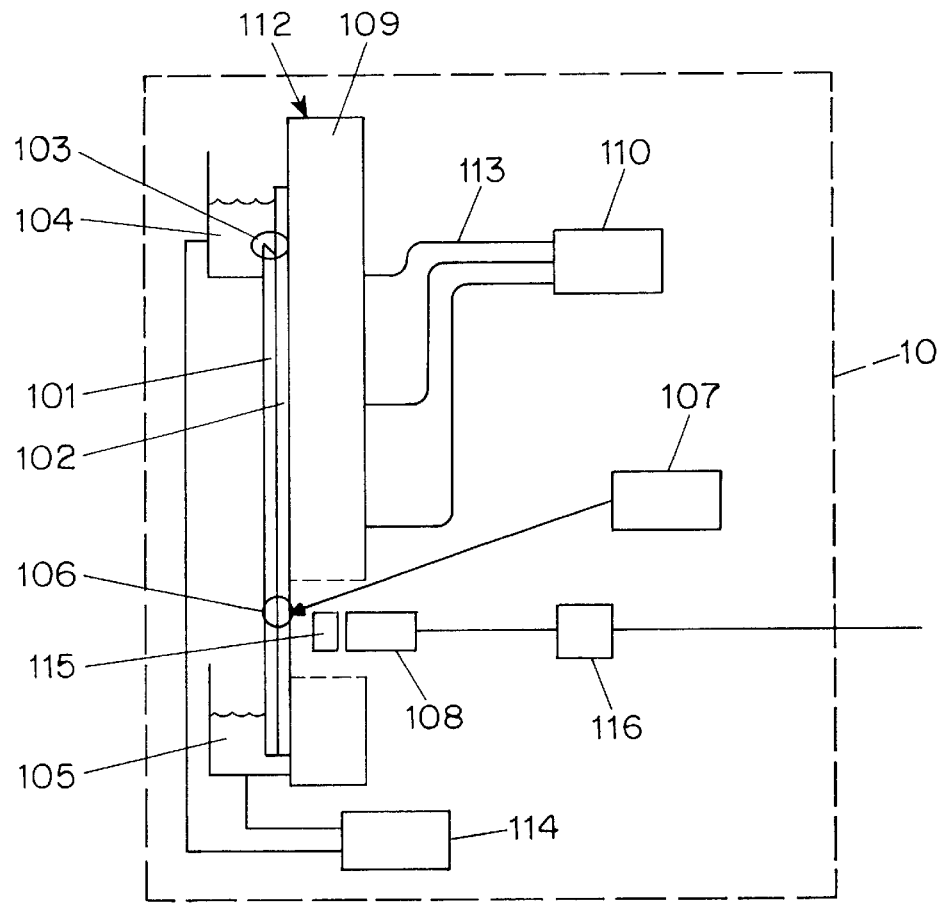
FIG. 1 shows a sectional side view of an apparatus according to the invention.

FIG. 1 shows a sectional side view of an apparatus in accordance with the present invention. The apparatus has a housing 10 within which the means for electrophoretic separation and detection of the sample are disposed. The housing 10 advantageously provides a sealed, light tight environment in which the processing of the sample is conducted.

Within the housing 10, a loaded electrophoresis gel 102 within a gel holder 101 is positioned on a mounting plate 109 which holds the gel in a fixed position relative to the remainder of the apparatus, including the excitation/detection portions of the apparatus. The loaded gel is advantageously held in place using suction through the mounting plate 109 generated using suction pump 110 and tubing 113, although other methods of holding the loaded gel in place may be used without departing from the spirit and scope of the invention.

Opposing ends of the loaded gel 102 are placed in contact with two electrodes, such as solution electrodes 104 and 105. These electrodes are connected to a power supply 114 which generates an electric field within the gel. This field causes the sample to migrate in the gel from loading site 103 towards detection site 106.

An excitation source 107 which supplies electromagnetic radiation having a frequency effective to excite the fluorophore used as a label is disposed within the housing 10 such that radiation from the excitation source 107 strikes the gel holder 101 at the detection site 106 causing any fluorophore labeled molecules at the detection site to emit light. This light is collected using optical system 115 and detected using detector 108. The analog output signal from detector 108 may then be converted to a digital signal using an A-to-D converter 116, and output for further processing and/or display.

The apparatus of the invention may be used with any type of electrophoresis gel and gel holder. Preferably, however, the apparatus is used with an ultrathin electrophoresis gel having a thickness of 25–250 microns of the type disclosed and claimed in commonly assigned U.S. patent application Ser. No. 08/332,577 which is incorporated herein by reference. Using such gels, in which the excitation/detection site is within about 12 cm of the loading site, it is possible to sequence up to 300 nucleotides (nt) in under 20 minutes. This is accomplished through the use of field densities of 100–400 volt/cm which are made possible by the improved heat dissipation which can be obtained using ultrathin gels. In addition, the voltage may be varied throughout any given sample run in order to allow maximum separation of sample.

Figure 2:
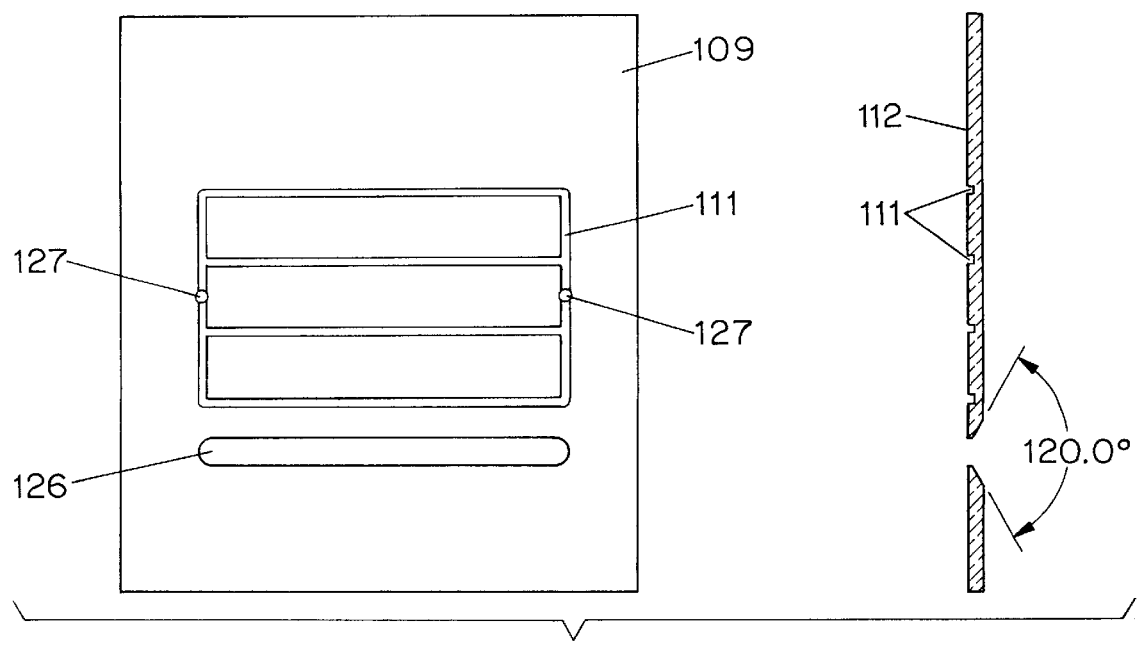
FIG. 2 shows a mounting plate for use in the present invention.

To enhance the heat dissipation which is achieved as a result of the use of thin gels, the present invention preferably makes use of a vacuum mounting technique. In this technique, as shown in FIG. 1, the gel holder 101 is mounted on a thermally conductive ceramic plate, 109, preferably made of alumina. FIG. 2 shows the structure of the mounting plate in more detail. As shown, the plate has an opening 126 cut to align with the detection site 106. This opening is preferably beveled so that it is wider on the side away from the gel mounting surface 112. The gel mounting surface 112 has canal 111 formed in it which is connected to vacuum pump 110 via ports 127 which are connected to tubing 113. The canal 111 is suitably about 0.1 inches wide (e.g. 0.092) and 0.05 inches (e.g. 0.047) deep, and is sealed over by the back substrate of the gel holder, 101, when properly mounted. The tight juxtaposition of the back substrate with the ceramic plate gives improved heat transference when compared to edge clamping devices. Vacuum sealing also allows for exquisite precision in focussing excitation sources, as described below.

A heat sink (not shown) consisting of an aluminum or other heat conducting metal sheet with extended fins may be contacted with the back face of the ceramic plate in order to improve heat conductance away from the gel.

The planar electrophoresis gel 102 generally contains a plurality of lanes for loading and detecting sample across the width of the gel. In many prior art devices, for example the device disclosed in U.S. Pat. No. 4,811,218, detection of various lanes is accomplished using a single detector which moves across the width of the gel and collects data from each lane in series. Because of the rapid progress of sample through the gel which is achieved using the present invention, (under 300 v/cm electric field, there is only about six seconds between oligonucleotides differing by one nucleotide), however, systems which require physical movement of a detector are inadequate to collect the data for each of the lanes. Improvements in the delivery of excitation energy and the detection of emitted energy therefore had to be made as part of the development of an effective apparatus and method for high throughput electrophoretic separations.

Delivery of Excitation Energy

Figure 3A:
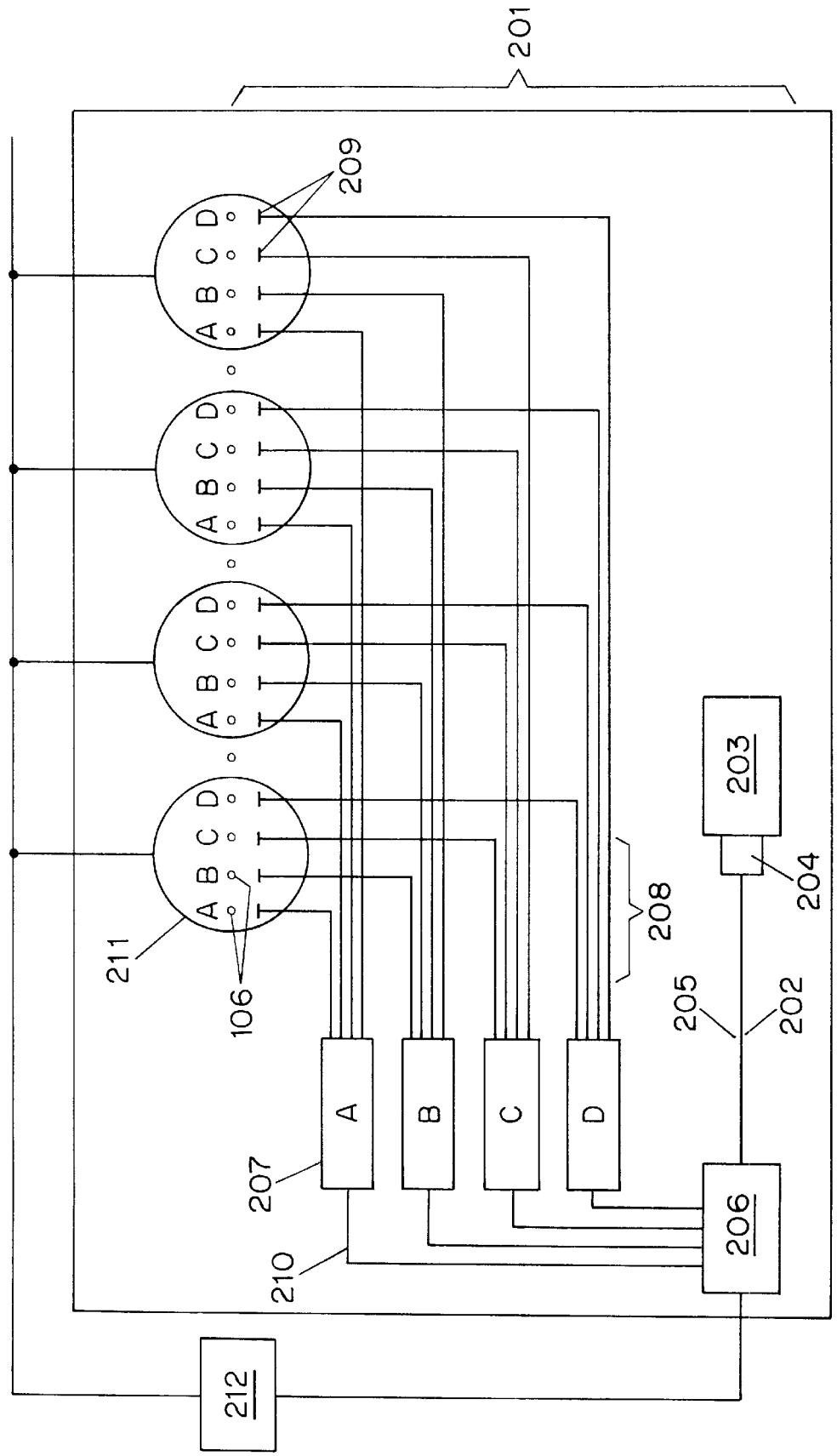
FIGS. 3A and 3B shows excitation and detection systems useful in the present invention.

In one embodiment of the invention, illustrated in FIG. 3A, excitation energy is conveyed to the excitation site by a fixed multiplexed fiber optic array, 201. Radiation, 202, from a source such as a laser, or light emitting diode, 203, is coupled, using a fiber launch or the like, 204, into an optical fiber 205. Suitable optical fibers for this purpose are fibers of 125 microns thickness with a core of 50 microns (if multimode) or preferably a core of 3.7 microns (single mode). The optical fiber carries the beam to a miniature board mountable switch, 206, that permits the switching of an optical signal from one output fiber 210 to another. For example, optical switching can be accomplished using a switch available from AMP, Inc., Harrisburg, Pa., in which a slight pivoting motion of a spherical mirror reflects the optical signal into one of two output fibers. The switch takes approximately 5–10 milliseconds to settle after each change. Several switches can be used in combination permitting the excitation beam to be divided into any number of output optical fibers 210.

As shown in FIG. 3A, four output fibers 210 are used to permit the sequential excitation of four groups of excitation/detection sites. The use of four output fibers is merely exemplary, however. In general, the apparatus of the invention will divide the incident light into from 2 to 10 groups.

Light in each output fiber 210 is conducted by the output optical fiber 210 to a beam splitter 207A, 207B, 207C or 207D which separates the beam into a plurality of final optical fibers 208, each conducting its respective fraction of the input excitation beam as an excitation beamlet. Each of the split optical fibers conveys the beamlet to a SELFOC® rod gradient index (GRIN) lens 209 (NSG America, Inc.; Somerset N.J.) which is fixed in location and disposed to irradiate its respective excitation site, 106, one lens for each excitation site. Experimental evidence shows that use of the vacuum seal to mount the gel holder also provides the advantage that the focal length of the GRIN lens can be exquisitely positioned with respect to the ultra-thin gel. The vacuum seal holds the gel extremely flat against the ceramic plate without the slight bowing or bending of gel holders found in edge clamped apparatuses.

The final optical fibers 208 and the lenses 209 are disposed to form a linear array of detection sites. Within this array, the final optical fibers 208 are ordered so that, when using four groups of excitation signals, every fourth detection belongs to the same group. The effect is that only a sub-set of excitation sites are irradiated at any one time (A, B, C, or D). Of course, if one were using two groups of excitation signals (only a single split of the incident beam 202), the final optical fibers 208 would be arranged in an alternating pattern (see FIG. 3B). This provides the advantage that a single detector, 211, may be employed to detect emissions from a plurality of excitation/detection sites if the detector output is synchronized with the switch so as to allow the signal processor to identify which signal came from which excitation/detection site.

The optical switch, 206, is programmed to switch the input laser beam into each of the output fibers 210 (and thus into the final optical fibers 208), for a period of preferably 20–100 milliseconds. Synchronization of the switch and detectors may be obtained with a microprocessor, 212.

The fixed multiplexed fiber optic array permits a high number of data points per second to be taken from each lane of the gel by conveying pulsed irradiation to each excitation site. Further, it permits use of a reduced number of detectors.

Figure 3B:
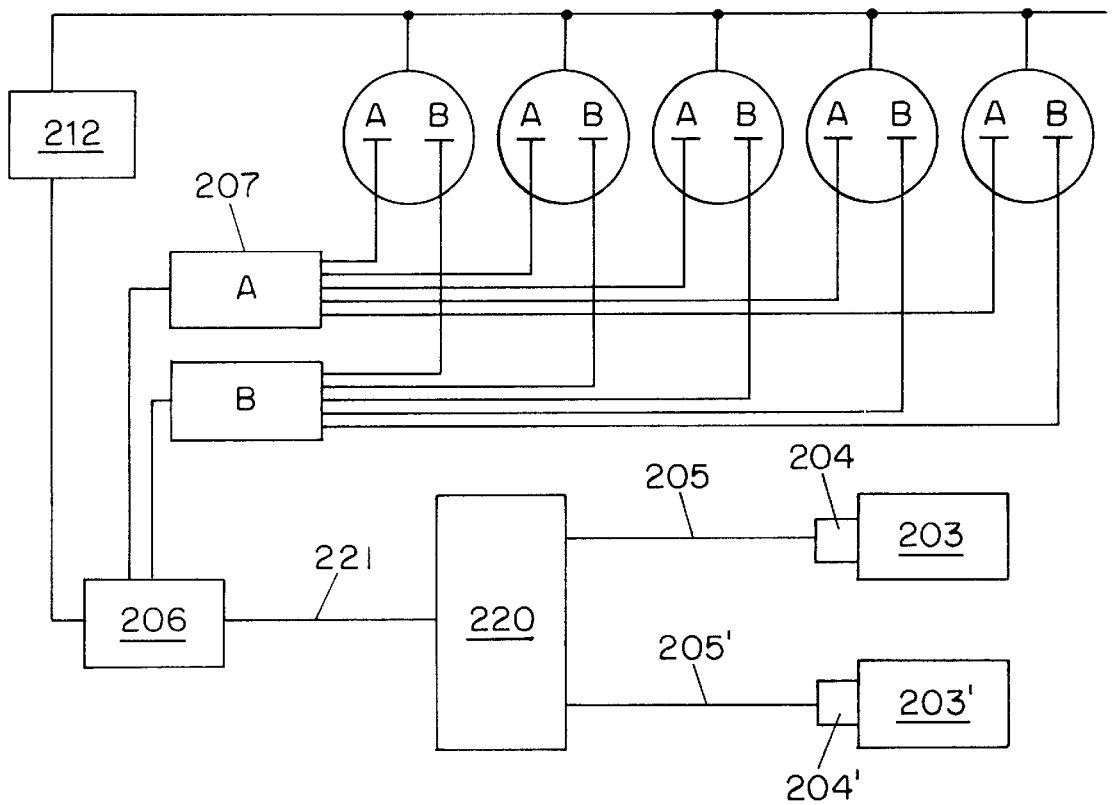

The fixed multiplexed fiber optic array can also be modified to bring different irradiation sources to the same excitation site in a series of alternating pulses as shown in FIG. 3B. Such an arrangement is constructed by employing different excitation sources 203 and 203', each coupled to an optical fiber 205 and 205'. An optical switch 220, operating in the opposite direction to switch 206 is employed to alternately select which source is to be conducted to the optical switch 206 via optical fiber 221. This arrangement permits multicolor fluorescence imaging for use when more than one fluorophore is used in any given lane of the gel.

Figure 4:
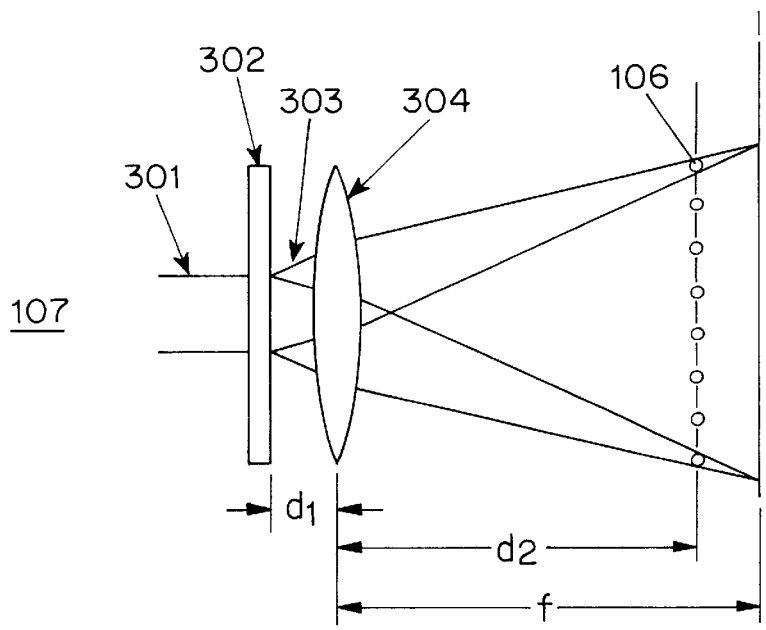
FIG. 4 shows a spot array generating grating system useful in the present invention.

In a second embodiment of the invention, illustrated in FIG. 4, radiation 301 from an excitation source 107 is directed to the excitation site 106 by use of a multiple beam splitter 302, such as a Spot Array Generation Grating which splits the incident beam into a number of beamlets, generally from 2 to 24 beamlets. Preferred diffraction gratings are of the type known as "transmissive" or "phase" gratings, because such gratings can be designed to produce an even intensity distribution of light among the resulting beamlets. In the illustrated embodiment, an incident laser beam of a frequency suitable for excitation of the fluorophore is directed into a binary phase grating, approximately 1 cm square, mounted on glass, thermo-plastic or the like of approximately ⅛th inch thickness (Semiconductor Technology Inc, Pointe Claire, Quebec). The transmitted beam is divided into a linear array of the desired number of excitation beamlets, 303, one for each intended excitation site, 106. The beamlets are directed to a focussing lens, 304 (e.g., Stock #G69, 129, Catalog 1994, Edmund Scientific). The focussing lens has in the embodiment shown preferably has a focal distance, f, of 505 mm. The spot at each excitation site can be varied in size by changing the distance, d, between the lens and the excitation site. The spots are suitably between 0.1 mm and 0.2 mm diameter. In a preferred embodiment, the spot array generation grating divides the incident laser beam into a linear array of 16 spots, and the lens is disposed between 200 to 500 mm from the gel.

As will be apparent to those skilled in the art, any excitation source can be used in embodiments utilizing a fiber optic array or a spot array generating grating, provided that the source is matched with the fluorophore to be used so that the radiation from the source excites the fluorophore to stimulate emission of detectable radiation. For example, the following non-limiting examples of commercially available excitation sources can be employed in the present invention: Optical lasers, e.g., Argon ion lasers, Argon krypton mixed gas lasers, Helium-neon lasers and doubled YAG lasers; Laser Diodes; Fiber (Solid State) Lasers; and Blue, Green, Red or infra red-Light Emitting Diodes (LEDs).

Figure 5:
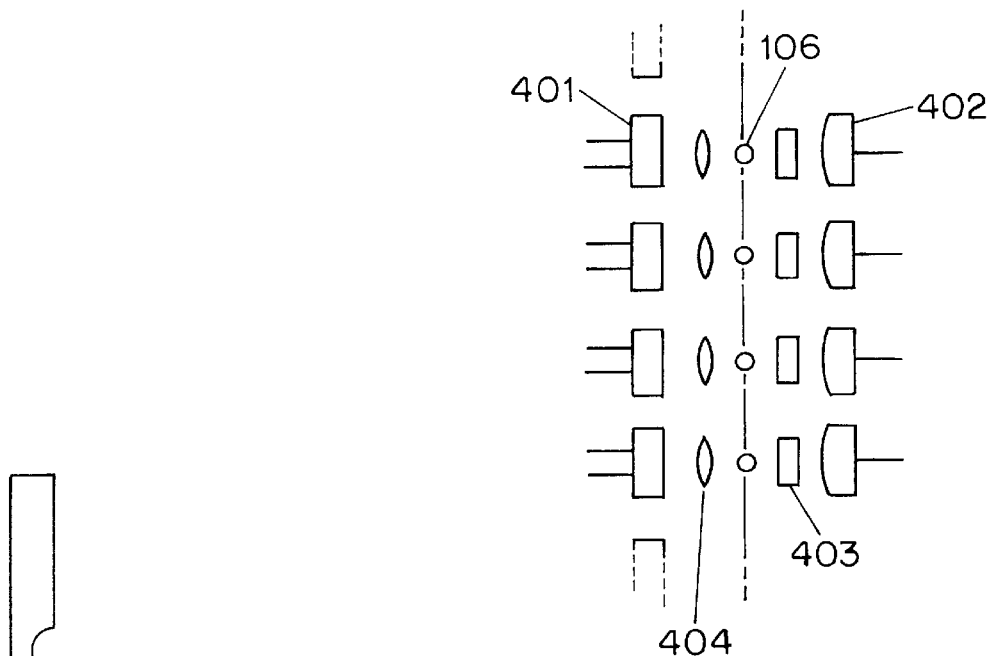
FIG. 5 shows an excitation and detection system employed in one embodiment of the present invention.

In a third embodiment of the invention, illustrated in FIG. 5, an independent excitation source is used for each excitation site. An effective and extremely low cost excitation source for this purpose is a light emitting diode for example those available from Stanley Corp. and identified as Type No. AN, BN, CN or DN. Unlike lasers, LEDs emit light in a broad band spectrum. Bandpass filters 403 disposed between the excitation/detection site 106 and the detector 402 should therefore be carefully selected to eliminate as much overlapping excitation irradiation from the detector as possible. One LED, 401, is disposed to irradiate each excitation site, 106, with or without a focussing lens 404 to focus the emitted radiation. An LED can emit 1.5–15 mW, sufficient to excite a population of fluorophores. In this embodiment, using an infra-red LED with Cy8 or Cy9 as a fluorophore, where the emitted light is in the infra-red region, the detector is preferably a photodiode detector 402.

While it is possible to have each LED 401 in the array constantly illuminated such that data collection from each lane can be continuous, it may be advantageous to use a pulsed excitation source in this embodiment as well. For example, where the lanes are close together, pulsing alternate lanes, or every fourth lane, may improve the accuracy of the detector by eliminating carry over form one lane to the next.

Fluorophores useful in the present invention are those which can be coupled to organic molecules, particularly proteins and nucleic acids and which emit a detectable amount of electromagnetic radiation in response to excitation by an available excitation source. As used herein, the term fluorophore encompasses materials having both fluorescent and phosphorescent emissions. It is desirable that the fluorophore exhibit a sufficient Stokes shift to permit filtering of emitted radiation from the excitation irradiation. A further limiting factor on the choice of fluorophore is whether the fluorophore contains functional groups that prevent it from surviving intact during the cleavage and deprotection reactions of commercially available oligonucleotide synthesis.

Suitable fluorophores for this invention include fluorescein and its analogs, rhodamine and its analogs, cyanine and related polymethines and their analogs, and the like. Specific fluorophores which are suitable for use with the present invention are Fluorescein isothiocyanate (FITC); 4-fluoro-7-nitrobenzofurazan (NBD-F); Texas Red® (Molecular Probes, Inc.; Eugene, Oreg.); tetramethyl rhodamine isothiocyanate (TRITC); and Cyanine dyes, especially, Cy5, Cy5.5 Cy7, Cy7.5, Cy8 and Cy9 (Biological Detection Systems, Pittsburgh, Pa.). Fluorescein fluorophores are preferably excited using an argon ion laser, while rhodamine fluorophores arc preferably excited using a helium neon laser. The cyanine dyes, which are described in U.S. Pat. Nos. 4,981, 977 and 5,268,486, which are incorporated herein by reference, are useful in combination with a red or infrared LED excitation source because the cyanine fluorophores Cy5 to Cy9 absorb and emit in the red and infra-red regions or laser diodes. Infra-red emissions are detected preferably with photodiodes, and particularly silicon photodiodes, 402, rather than PMTs.

An alternative to using LEDs in the above embodiment is use of laser diodes. Red and infra-red laser diodes can be used to excite fluorophores such as Cy5, Cy5.5, and Cy7.

Detection of Fluorophore Emitted Radiation

Emissions from the fluorophores are detected by a detector disposed to receive radiation from the detection site.

Figure 6:
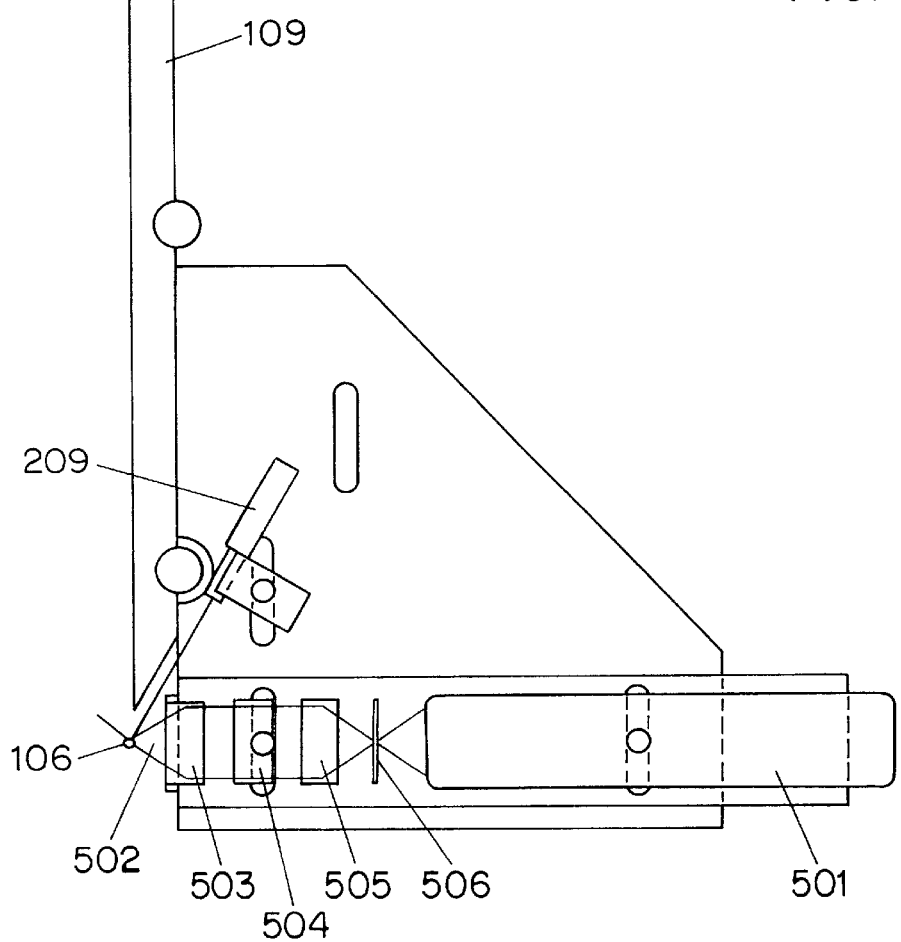
FIG. 6 shows a detection system useful in the present invention.

FIG. 6 illustrates a first embodiment, particularly suited for use with a fixed multiplexed fiber optic array. A linear array of detectors 501, is disposed to receive emissions 502, from a linear array of detection sites 106. A detector may be any two dimensional detector, such as a CCD, a photodiode or, in the preferred embodiment, a photomultiplier tube (PMT). Disposed between the detection site and the PMT are a collecting lens 503, a bandpass filter 504, a focussing lens 505, and a spatial filter 506. The bandpass filter is an interference filter (Omega Optical, Inc. Brattleboro, Vt.) or the like of 20 to 40 nm transmission wavelength width chosen to transmit the fluorescence emission and to block reflected light of the excitation source. The spatial filter is chosen to optimize recognition of the band of fluorophore-labeled sample as it passes through the detection site. Elimination of fringes and tails of bands using a spatial filter tends to increase the signal to noise ratio of the detected signal. Preferred spatial filters are rectangular in shape with a height of 100 microns and width of 250 microns.

The detector collects a signal, which is integrated over a finite time-span and converted to a digital output. A suitable integration time for the invention is 5–100 milliseconds. When a PMT is used to record a plurality of excitation/detection sites, the width of the PMT is selected in a manner consistent with the number of sites. In general. PMT's with width of from 3–15 mm, and preferably about 5 mm are suitable. In this case, the integration of signal must be synchronized with the multiplexing switch of the excitation irradiation source. Such synchronization can be controlled by a microprocessor 212. As stated above, a suitable period of multiplex switching is 20–100 milliseconds, although any period that results in a sufficient number of data points for analysis can be used. Fluorescence emissions can therefore be correlated with the respective detection site on the gel. Fluorophore must be chosen such that the delay in fluorescence emission from an old detection site does not cause significant overlap with the new fluorescence emissions from a new detection site.

In another embodiment, if multiplexed excitation beams are not used, then a single detector is required for each detection site. Any type of detector may be employed, such as CCDs, PMTs or silicon photodiodes (Series S2386 or S2387; Hamamatsu Photonics KK, Hamamatsu City, Japan). The silicon photodiode 601 is disposed at the focal distance of the lens of the diode 603 from the apparent detection site 106 and to collect emitted light 602 in a position out of alignment with the excitation beam as illustrated in FIGS. 7A and 7B.

Figure 7A:
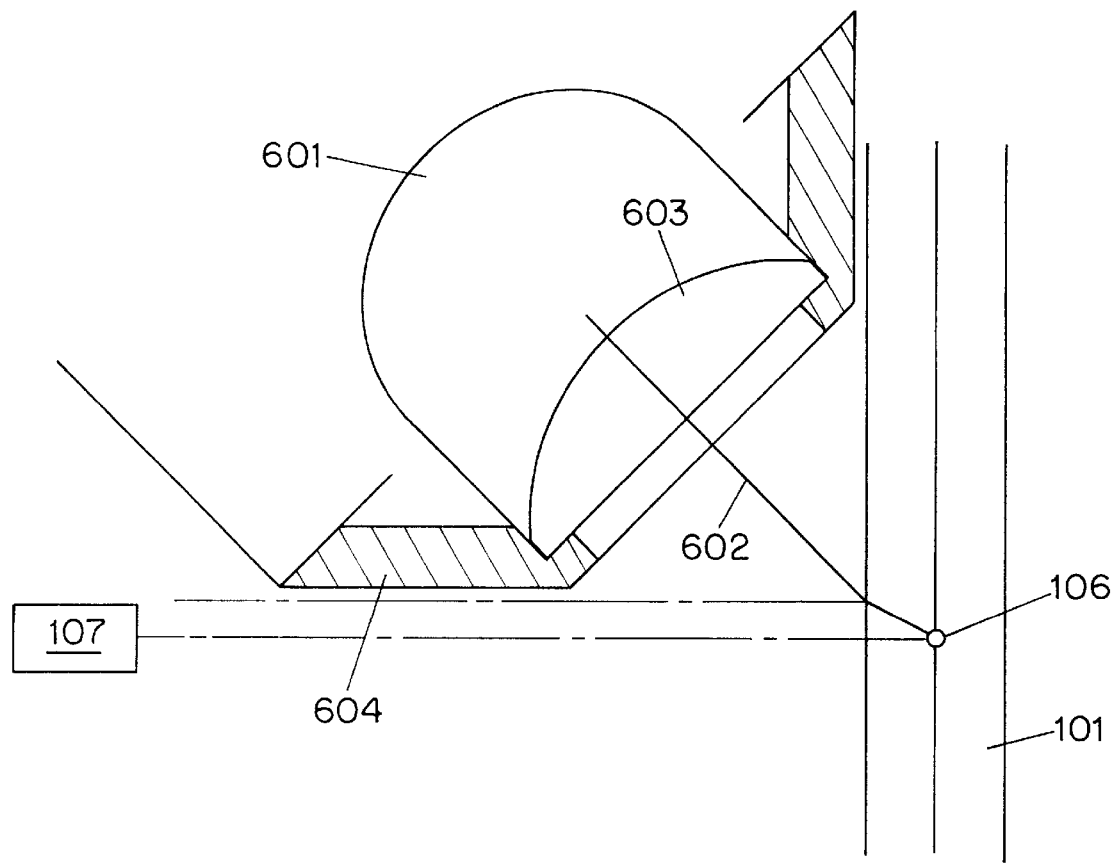
FIGS. 7A and 7B show an alternative detection system useful in the present invention.

In FIG. 7A, the light 107 from the irradiation source is directed to the excitation site along the horizontal axis of the gel. A linear array of detectors can be positioned both above and below said axis in diode holders 604. Thus, if a first linear array of detectors is focussed at excitation sites staggered from the excitation sites recorded by the second linear array of detectors, it is possible to utilize twice as many excitation spots per gel. Further, a linear array of detectors may be disposed on the opposite side of the gel, again above or below the horizontal axis of the gel. If all detectors detect excitation sites staggered from each other, it is possible to detect at least four excitation sites for every unit of detector width.

Figure 7B:
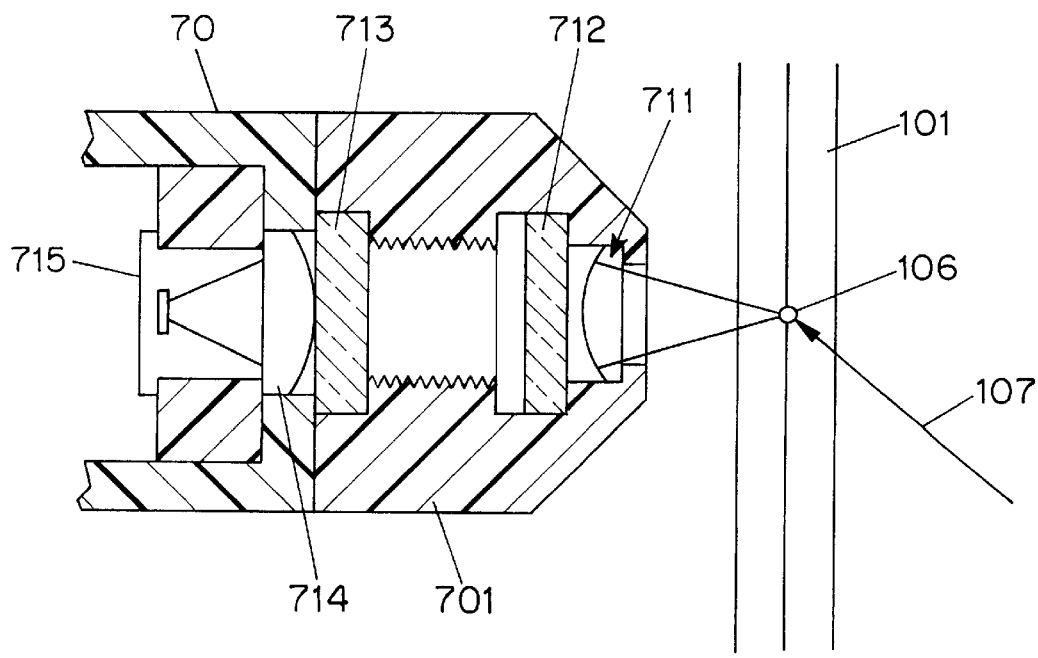

FIG. 7B shows an alternative embodiment of a photodiode detector useful in the invention. Light 107 from the excitation source impinges on the gel holder 101 at an angle relative to the surface of the gel holder. The detector element 70 collects light which is emitted substantially perpendicular to the surface of the gel holder 101. The detector element 70 has a body member 701 in which a AR-coated (antireflective) aspherical lens 711, two AR-coated cut-off filters 712 and 713 selected to transmit light of the emitted wavelength, a second AR-coated aspherical lens 714 and a photodiode 715 are mounted. A spacing between the filters (~½ to ¾ inch) may be used to reduce background radiation reaching the photodiode 715, since radiation which is not directed straight into the detector is absorbed by the interior of the body member 701.

All signals received from detectors are preferably converted from analog to digital and conveyed to a serial port for transmission to a multipurpose computer for storage and for further processing and analysis. It will be understood, however, that the analog output could be sent directly to an output device for display or printing.

Figure 8:
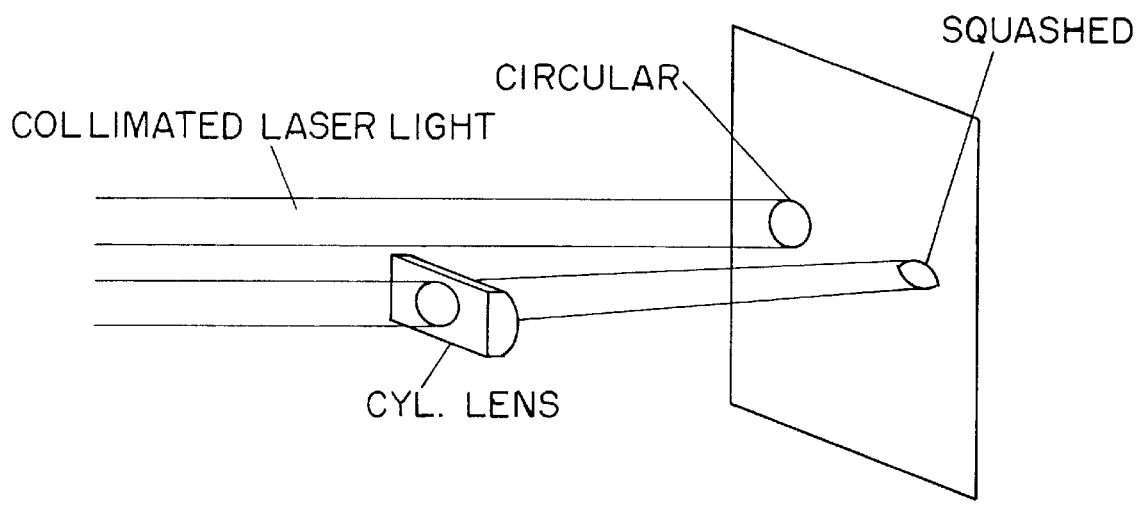
FIG. 8 shows a squashed excitation beamlet obtained using a cylindrical lens.

In selecting a combination of optics for use in the apparatus of the present invention, it may be advantageous to use a lens to concentrate the excitation beam into a smaller area within the detection zone. In particular, it may be desirable to use a cylindrical lens which reduces the dimension of the excitation beam in one direction (e.g. vertical) while leaving it unaltered in the other (horizontal) direction. (FIG. 8) Such a "squashed" excitation beam can increase the resolution of the apparatus since a shorter length of the electrophoresis gel is interrogated.

Figure 9A:
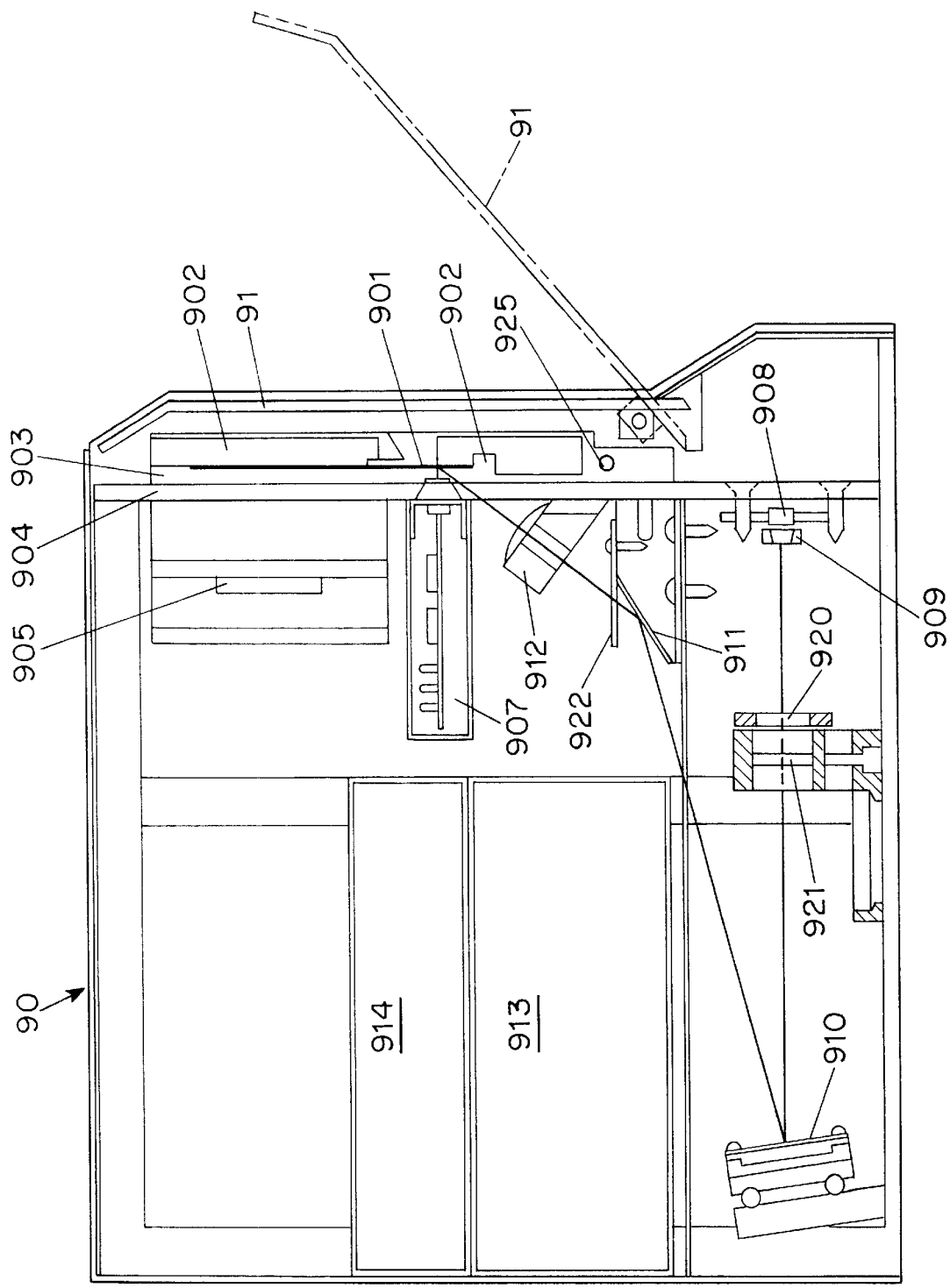
FIGS. 9A, 9B and 9C show a further embodiment of the invention.

FIG. 9A shows a cross-section view of a preferred embodiment of the present invention. The various components of the apparatus are disposed within a housing 90, which has a access door 91 the front thereof. The access door 91 is hinged to permit movement between a closed position (solid line) and an open position (dashed line).

Within the housing 90, the gel holder 901 is held in position between two solution electrodes 902, 902' against mounting plate 903. The mounting plate 903 and the solution electrodes pivot outward on pin 925 to facilitate loading of an electrophoresis gel. A heating element 904 is disposed in thermal contact with the back surface of the mounting plate 903 to permit heating of the gel. A fan 905 which is surrounded to a sub-housing 906 and vented to the exterior of the housing 90 blows room temperature air across the back of the heating element 904. Through a combination of heating and cooling provided by the heating element 904 and fan 905, respectively, a desired temperature in the range of from 30 to 55 degrees C. can be maintained to a tolerance of 0.5 degrees.

Figure 9B:
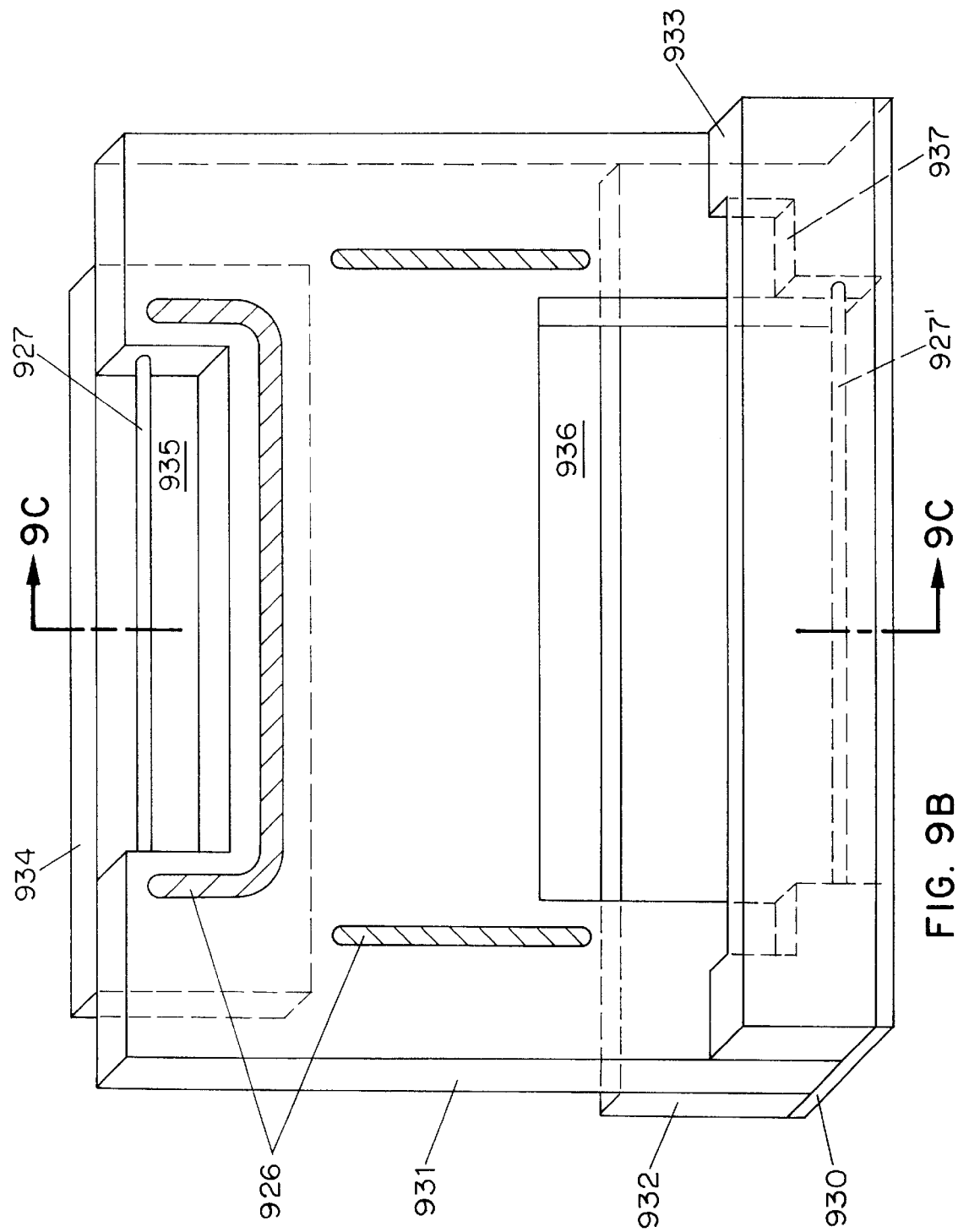
Figure 9C:
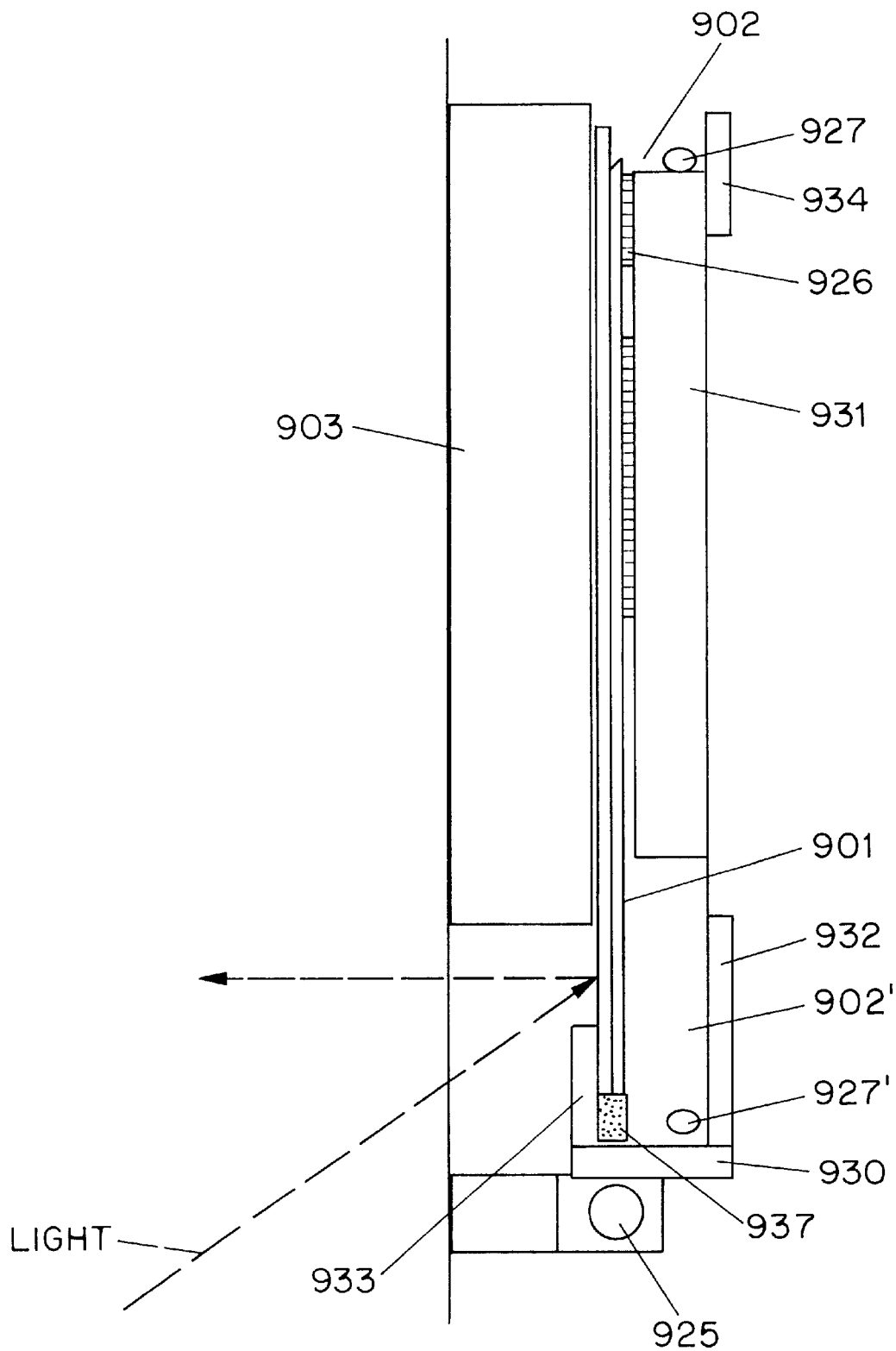

FIGS. 9B and 9C show the mounting of the gel within the apparatus of FIG. 9A in greater detail. FIG. 9B shows the electrode assembly when viewed from the inside. The assembly is formed from a base plate 930, a main body portion 931, and three reservoir wall portions 932, 933 and 934, all formed from plastic. The body portion 931 has a first reservoir opening 935 cut in the top edge thereof and a second reservoir opening 936 cut in the bottom edge thereof. Reservoir wall portion 934 entirely covers the outside face of reservoir opening 935 to partially define the upper solution electrode 902, while reservoir wall portion 932 at least partially covers the outside face of reservoir opening 936.

Reservoir wall portion 933 is disposed on the interior surface of the of the body portion 931. Reservoir wall portions 932 and 933, the base plate 930 and the body portion 931 together define the lower solution electrode 902'. Reservoir wall portion 933 has a stepped region 937 within the lower solution electrode on which the edges of the gel holder rest when in place. Wires 927, 927' extend across both solution electrodes 902, 902' to provide the electric field for electrophoresis.

In use, as shown in FIG. 9C, the gel holder 901 is placed on set portions 937 of the reservoir wall member 933 so that the beveled edge is submerged within the upper solution electrode 902 when it is filled with buffer. The electrode assembly is then tipped back into the apparatus so that the gel holder 101 is sandwiched between the body member 931 and the mounting plate 903, and held tightly in place using knurled knob screws. Gasket materials 926 disposed around the first reservoir opening 935 and on the interior surface of the body member 931 act to seal the upper solution electrode 902 and to cushion the pressure on the gel holder 101. Buffer is added to the solution electrodes 902 and 902' and the sample is then loaded onto the gel through the beveled opening.

A detector module 907 (FIG. 9A) consisting of a linear array of photodiodes such as those shown in FIG. 7B, each connected to a circuit board is aligned with the excitation detection site in the gel, and collects light which is emitted perpendicular to the surface of the gel holder 901. The circuit board contains an analog-to-digital (A/D) converter which converts the analog current output of the diode to a digital voltage signal. This digital signal may then be further processed by the computer circuit board 914 disposed within the housing or transmitted to an external computer for processing.

Figure 11:
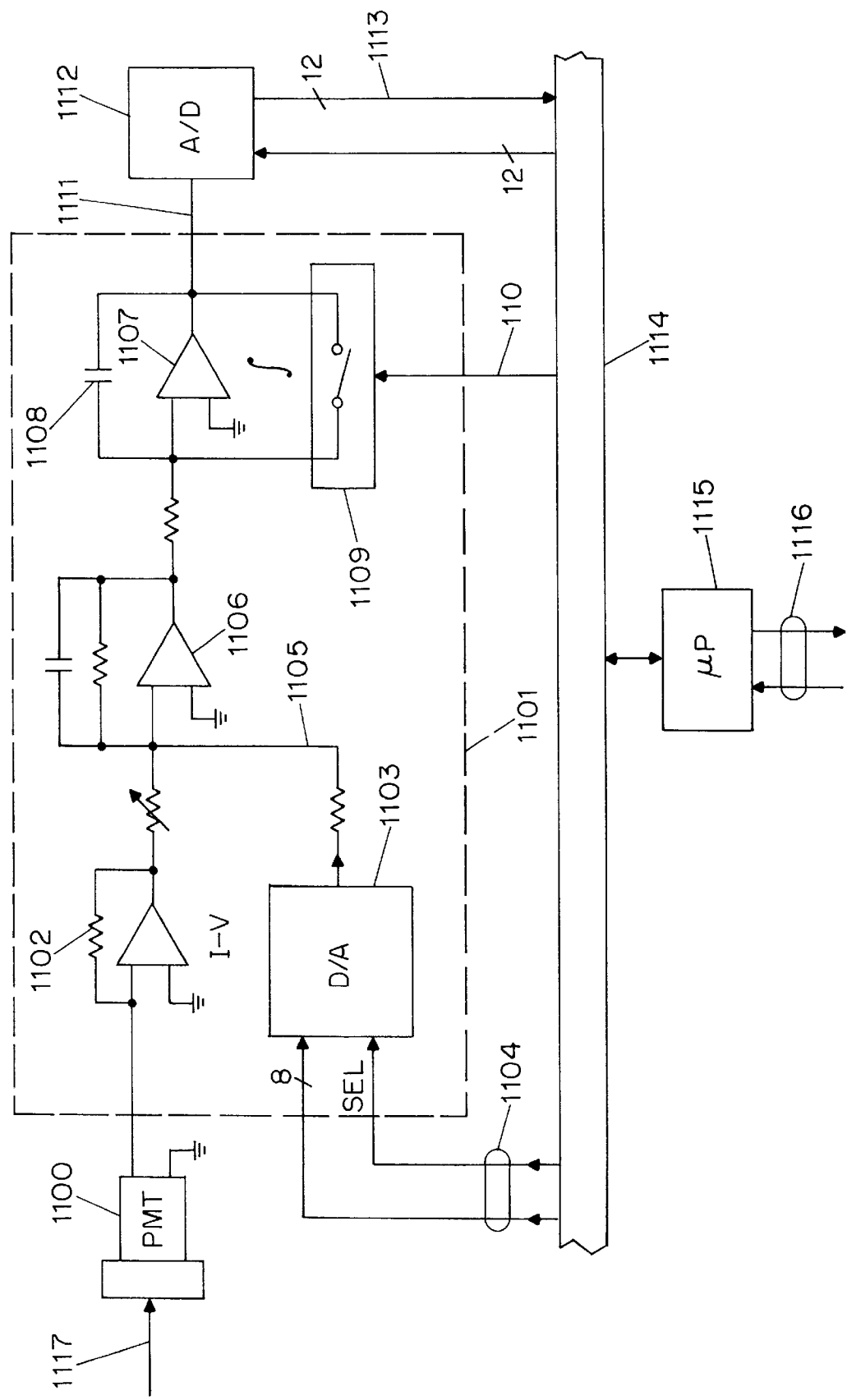
FIG. 11 shows a preferred A/D converter circuit.
Figure 12A:
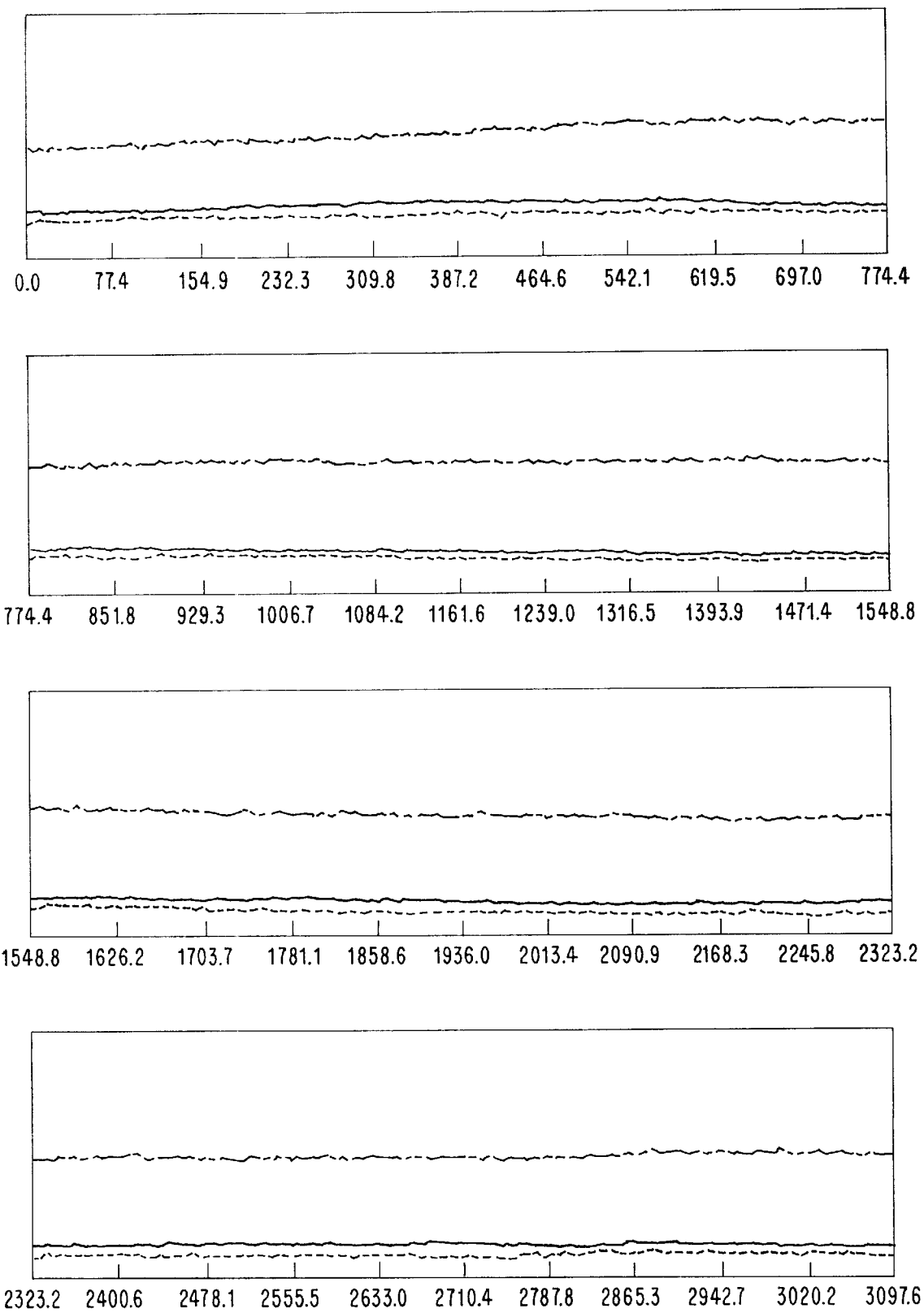
FIGS. 12A–12E shows the output of a photomultiplier tube when sequencing M13 using an apparatus of the invention.
Figure 12B:
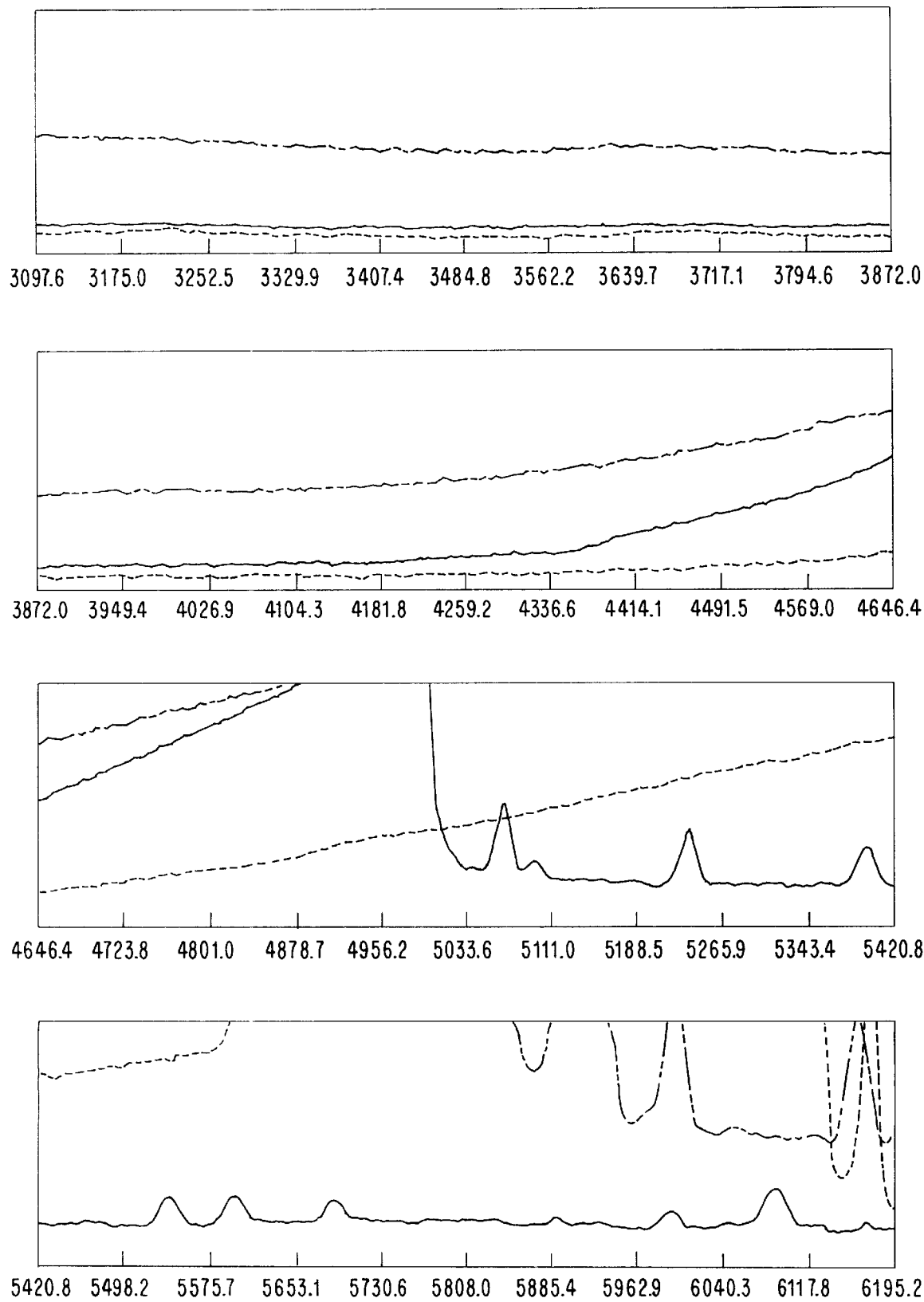
Figure 12C:
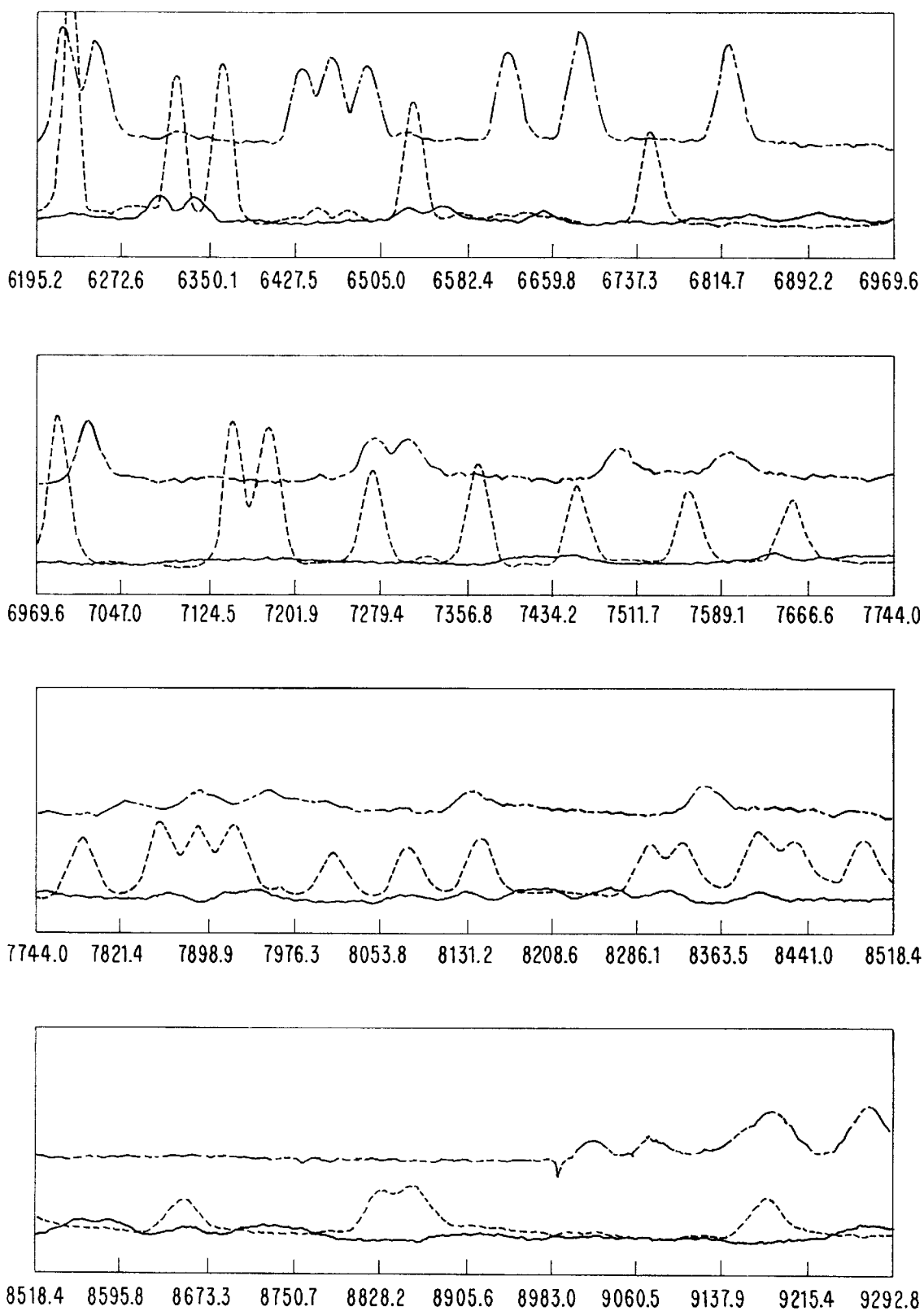
Figure 12D:
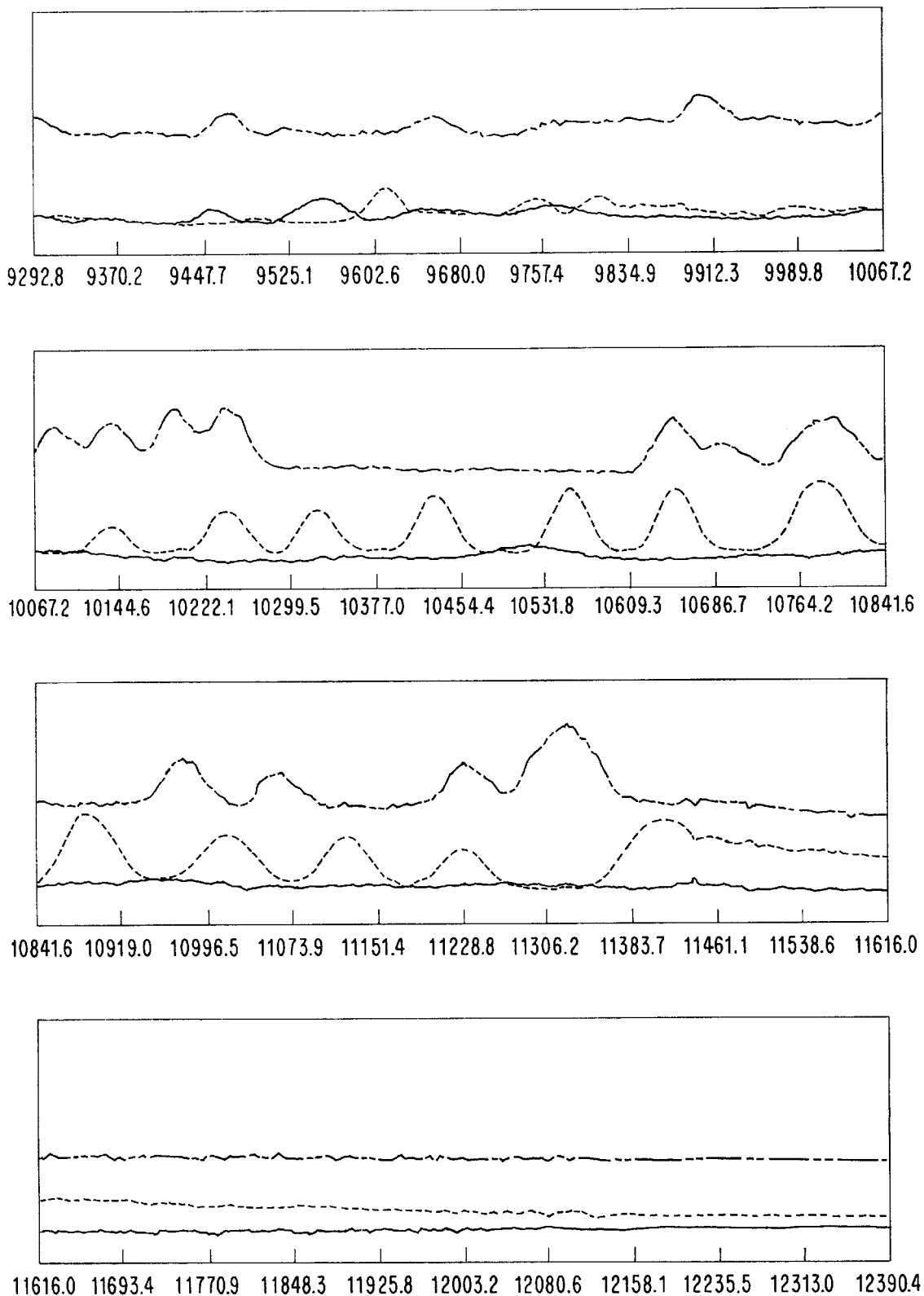
Figure 12E:
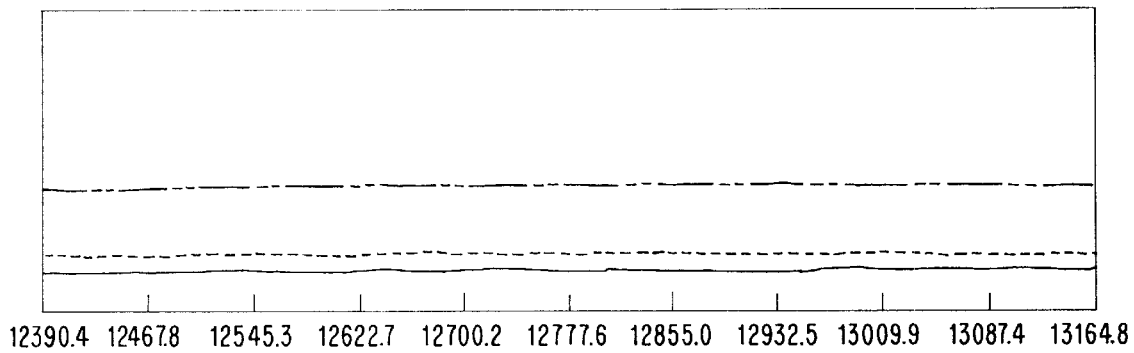
Figure 12E:
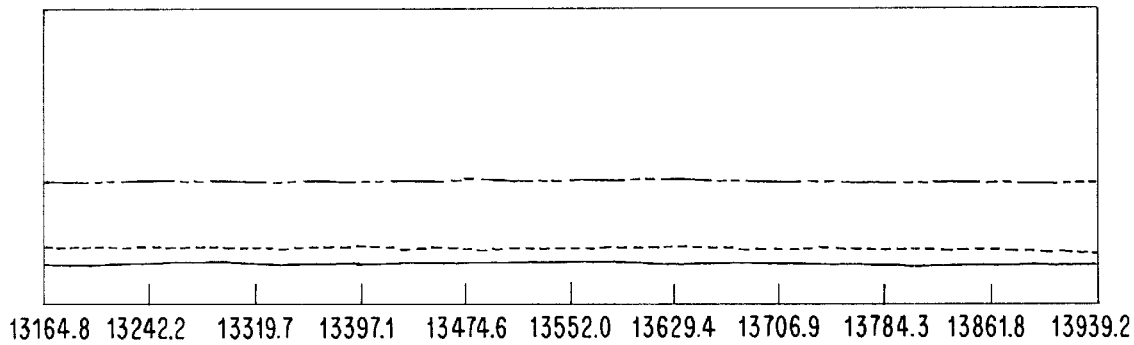
Figure 12E:
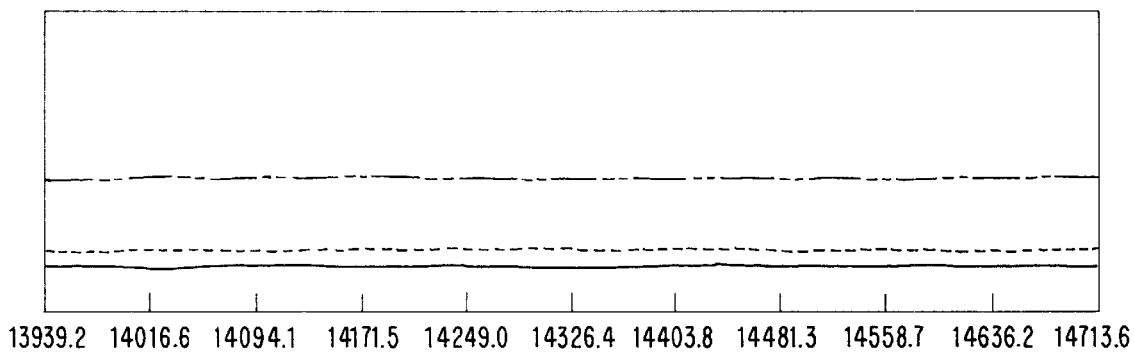
Figure 12E:
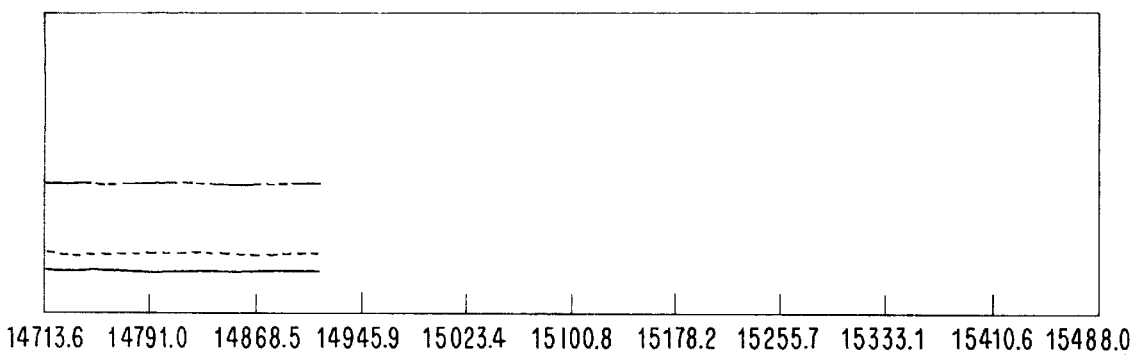

While essentially any convention A/D converter can be employed in the apparatus of the invention, preferred A/D converters are of the type described in U.S. patent application Ser. No. 08/452,719 which is incorporated herein by reference. Briefly, in such a device as shown in FIG. 11, an eight-bit digital-to-analog converter (D/A) 1103 is provided, which generates an output on line 1105. The output of the D/A is controlled by processor 1115 through digital bus 114. Digital bus 114 provides a select line and eight data lines 104 to the D/A 1103. In this way, the processor 1115 can provide an offset or base level for the signal being processed.

The programmed offset from D/A 103 and the voltage level from amplifier 1102 are summed and amplified by op amp 1106. The output of op amp 1106 is then provided to integrator 1107, which comprises an op amp, a highly stable capacitor 1108, and related components. Integrator 1107 is controllable with respect to the starting and ending time of its integration periods by analog switch 1109, controlled by discrete control line 1110. The output of the integrator 1107 is provided to A/D 1112. A/D 1112 is preferably a multiple-input A/D, and only one of its inputs is shown in FIG. 11 for clarity. A/D 1112 has a serial control line 1127 and a serial data line 1113, which carries 12 bits of data from the A/D conversion process. Processor 1115 has a bidirectional serial link 1116 with a personal computer or work station omitted for clarity in FIG. 11.

In an apparatus incorporating an A/D circuit of this type, the dynamic range of the A/D 1112 is not spread out over the entire range of possible outputs from the detector 1100. Instead, the offset from D/A 1103 is used to set a base level which is the starting point for the dynamic range of the A/D 1112. In addition, the integration periods, namely periods during which switch 1109 is open so that integration takes place, are sometimes short and sometimes long. Shortening the integration period permits the A/D 1112 to extract meaningful data even at times when the photon flux along path 1117 is very high, much higher than the flux during times when a tagged nucleotide is present in the sensing area.

The excitation beam is provided by a laser diode 908 mounted in alignment with an aspherical lens 909. The aspherical lens 909 collimates the output from the laser diode 908 and directs it towards a transmissive diffraction grating 920 which divides the light from the laser diode into 16 beamlets of substantially equal intensity. These beamlets are conducted by lens 921 and mirrors 910, 911 to a cylindrical lens 912 which forms the squashed spots at the excitation/detection sites. The mirrors 910, 911 may be aluminum or aluminum coated glass when the excitation wavelength is below 650 nm, but are advantageously gold coated glass when for loner wavelengths because of the greater reflectivity of gold at these wavelengths. Dielectric mirrors may also be used although they are substantially more expensive.

Figure 10:
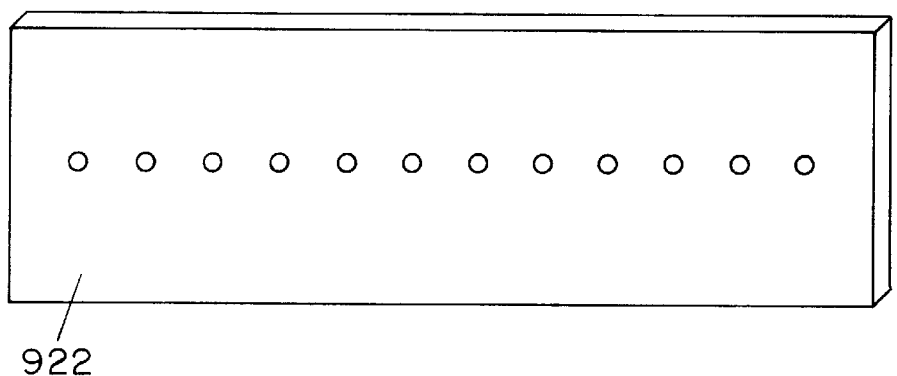
FIG. 10 shows an apertured barrier useful in the apparatus of the invention.

Within the apparatus shown in FIG. 9, there is also an apertured barrier 922 of the type shown in FIG. 10 between the last mirror 911 and the cylindrical lens 912 aligned so that each beamlet passes through an individual hole (1–3 mm diameter) in the barrier. This barrier reduces the amount of scattered light which reaches the excitation detection site.

A power supply 913 is disposed within the housing 90 and is connected to the solution electrodes 902 to provide the voltage gradient for electrophoresis.

The sequencing apparatus of the invention can provide a signal directly to a dedicated computer, for example a personal computer, for processing an sequence analysis. For many applications, however, improved performance at reduced cost can be obtained by connecting a number of sequencing apparatus to a single computer in a network configuration. For example, several sequencers can be connected into a network as described in concurrently filed U.S. patent application Ser. No. 08/570,994, (Attorney Reference No. VGEN.P-004-US), now U.S. Pat. No. 5,776,767 which is incorporated herein by reference. In this case, the apparatus of the invention will also suitably include an on-board computer board 915 containing a buffer memory of sufficient size to store substantial portions of the data from a sequencing run and a microprocessor for controlling the acquisition of data and the subsequent transfer of this data to a shared network computer for sequence analysis processing.

It will be appreciated that the apparatus shown in FIG. 9 may incorporate additional features without in any way departing from the present invention. For example, a light may be placed inside the housing which illuminates the gel holder when the access door 91 is in the open position to facilitate loading of the apparatus. Similarly, status lights and indicators may be disposed on the lower portion of the housing to indicate parameters such as the duration of an on-going sequencing operation. The apparatus of FIG. 9 can also be used with an external light source such as a laser and an optical train (for example fiber optics or mirrors) to direct the light from the source to the aspherical lens 909.

EXAMPLE

A single stranded M13 DNA molecule is hybridized to FITC labeled universal primer. Sequencing reactions are undertaken using SEQUENASE™ in the recommended reaction buffers. After completion of reactions, loading buffer of xylene cyanol, bromophenol blue and glycerol is added to the reaction tubes to provide a visible loading marker. A microgel, prepared as disclosed in U.S. patent application Ser. No. 08/332,577 is mounted on an alumina plate by vacuum seal. A solution electrode is affixed such that the upper chamber contacts the upper end of the gel, and the lower chamber contacts the lower end of the gel. GRIN lenses, each attached to its respective optical fiber of a fiber optic array are disposed at the focal length from the excitation site near the lower end of the gel. An argon ion laser of 5 mW power output, 488 nm wavelength is directed into the optical fiber by the fiber launch (upstream from the beam splitter). A linear array of PMTs is disposed to receive fluorescence emissions from the detection sites, one PMT per detection site. The M13 sample is loaded into the loading site. An electric field of 250 v/cm is suspended across the gel. Electrophoresis of the sample through the gel is recorded and displayed as in FIGS. 12A–12E, where the x-axis shows time in tenths of seconds. The data shows clearly resolved M13 sequence data out to 220 nt in 12 minutes.

We claim:

1. An apparatus for electrophoretic separation and real-time fluorescence detection of a plurality of samples labeled with a fluorophore comprising:

(a) a housing for receiving an electrophoresis gel loaded at a plurality of loading sites with the samples;

(b) means for applying an electric field to a gel received within the housing to cause the samples to migrate within the gel from the loading sites to a plurality of detection sites;

(c) a source of electromagnetic radiation having a wavelength effective to induce fluorescent emission from the fluorophores;

(d) means for sequentially delivering the electromagnetic radiation to a plurality of pre-defined groups of detection sites, each group containing at least two detection sites;

(e) means for detecting fluorescent emission from the fluorophores, and (f) means for correlating detected emission with the detection sites to which the electromagnetic radiation is delivered whereby a given emission is linked to the detection site being irradiated.

2. An apparatus for electrophoretic separation and real-time detection of a sample labeled with a fluorescent label comprising (a) a housing for receiving an electrophoresis gel holder;

(b) a plurality of excitation sources of electromagnetic radiation having a wavelength effective to excite the fluorescent label arranged in an array to deliver excitation energy to each of a plurality of excitation sites on an electrophoresis gel holder disposed within the housing;

(c) means for applying an electric field of from 100 to 400 V/cm to a gel holder received within the housing for separation of a sample applied to a gel within the holder;

(d) a plurality of detectors arranged in an array to detect emitted light from each of the plurality of excitation sites; and (e) means for excluding from the detectors electromagnetic radiation of the wavelength delivered from the excitation sources.

3. An apparatus for electrophoretic separation and real-time detection of a plurality of samples each comprising a mixture of fluorescently-labeled polynucleotides, said apparatus comprising:

(a) a holder for receiving a flat separation matrix of sufficient width to accommodate a plurality of parallel separation lanes and holding it in a fixed position within the apparatus;

(b) means for applying an electric field to a separation matrix received within the holder, whereby samples loaded onto the separation matrix are caused to migrate from a plurality of origination sites through the separation matrix to a plurality of detection sites;

(c) excitation means for providing excitation energy to the detection sites, said excitation energy having a wavelength effective to induce emission from the fluorescently-labeled polynucleotides and said excitation means directing excitation energy substantially perpendicular to a flat major surface of the separation matrix received within the holder; and (d) detection means for detecting emission from the fluorescently-labled polynucleotides as they pass through the detection sites, wherein all of the components of the excitation means and the detection means are maintained in a fixed position relative to the separation matrix during separation and real-time detection.

4. An apparatus for electrophoretic separation and real-time fluorescence detection of a sample comprising:

(a) a housing adapted to receive an electrophoresis gel holder;

(b) an excitation source of electromagnetic radiation;

(c) means for delivering electromagnetic radiation from the excitation source to each of a plurality of pre-defined excitation/detection sites within a linear array of excitation/detection sites on a gel holder disposed within the housing;

(d) means for applying an electric field for to a gel holder disposed within the housing for separation of a sample applied to a gel within the holder;

(e) means for detecting emissions from the sample at the excitation/detection site, wherein the housing holds the gel holder in a fixed position relative to the means for delivering electromagnetic radiation and the means for detecting emissions when the gel holder is disposed within the housing;

(f) a thermally conductive mounting plate; and (g) means for vacuum affixing the gel holder to the mounting plate.

5. An apparatus according to claim 4, wherein the mounting plate is formed from a ceramic.

6. An apparatus according to claim 4, wherein the mounting plate is alumina.

7. An apparatus for electrophoretic separation and real-time fluorescence detection of a sample comprising:

(a) a housing adapted to receive an electrophoresis gel holder;

(b) an excitation source of electromagnetic radiation;

(c) means for delivering electromagnetic radiation from the excitation source to each of a plurality of pre-defined excitation/detection sites within a linear array of excitation/detection sites on a gel holder disposed within the housing;

(d) means for applying an electric field to a gel holder disposed within the housing for separation of a sample applied to a gel within the holder; and (e) means for detecting emissions from the sample at the excitation/detection sites, wherein the housing holds the gel holder in a fixed position relative to the means for delivering electromagnetic radiation and the means for detecting emissions when the gel holder is disposed within the housing, and wherein the means for delivering electromagnetic radiation from the excitation source to each of a pre-defined group of excitation/detection sites comprises a plurality of optical fibers for delivering electromagnetic radiation from the excitation source to a linear array of excitation/detection sites on the gel holder, optical switching means for sequentially directing electromagnetic radiation into each of several pre-defined groups of the optical fibers, each group including at least two optical fibers for delivering electromagnetic radiation to at least two spatially separated excitation/detection sites within the array; and means for correlating a detected emission with the switching of the excitation electromagnetic radiation such that a given emission may be linked with the excitation/detection site being irradiated.

8. An apparatus according to claim 7, wherein the detection means comprises at least one photomultiplier tube aligned to receive light from a plurality of adjacent excitation/detection sites within the array.

9. An apparatus according to claim 7, wherein the means for applying an electric field is a power supply for providing an electric field of 100–400 V/cm to a gel within the holder.

10. An apparatus according to claim 7, wherein the excitation source is a laser.

11. An apparatus according to claim 7, wherein the excitation source is a plurality of light emitting diodes.

12. An apparatus according to claim 7, wherein the excitation source is a laser diode.

13. An apparatus according to claim 7, wherein the means for detecting emission is an array of photomultiplier tubes.

14. An apparatus according to claim 7, wherein the means for detecting emission is an array of photodiodes.

15. An apparatus according to claim 14, wherein the photodiodes are silicon photodiodes.

16. An apparatus according to claim 7, wherein the means for delivering electromagnetic radiation from the excitation source delivers said energy to a major surface of an electrophoresis gel disposed within the gel holder.

17. A method for electrophoretic separation and real-time fluorescence detection of a plurality of samples labeled with a fluorophore comprising the steps of:

(a) loading the samples onto a plurality of lanes of an electrophoresis gel at a plurality of loading sites;

(b) applying an electric field to the loaded gel such that the samples migrate through the gel from the loading sites to a plurality of detection sites;

(c) delivering electromagnetic radiation having a frequency effective to induce emission of electromagnetic radiation from the fluorophore sequentially into each of a plurality of pre-defined groups of detection sites, each group including at least two detection sites;

(d) detecting emission from the detection sites while the sample is migrating through the gel; and (e) correlating detected emission with the detection sites to which the electromagnetic radiation is delivered whereby a given emission is linked with the detection site being irradiated.

18. A method according to claim 17, wherein the electromagnetic radiation is delivered using a laser.

19. A method according to claim 17, wherein the electromagnetic radiation is delivered using a plurality of optical fibers.

20. A method according to claim 17, wherein the fluorophore used is fluorescein and the electromagnetic radiation delivered is 488 nm light from an argon ion laser.

21. A method according to claim 17, wherein the fluorophore used is rhodamine and the electromagnetic radiation delivered is from a helium neon laser.

22. A method according to claim 17, wherein the fluorophore used is Cy5.5 and the electromagnetic radiation delivered is from a laser diode.

23. A method according to claim 17, wherein the sample labeled with a fluorophore is an oligonucleotide.

24. A method according to claim 17, wherein the electric field applied is from 100 to 400 V/cm.

25. A method for electrophoretic separation and real-time detection of a sample labeled with a fluorophore, comprising:
(a) loading the samples onto a plurality of lanes of an electrophoresis gel at a plurality of loading sites;
(b) applying an electric field to the loaded gel such that the samples migrate through the gel from the loading sites to a plurality of detection sites;
(c) dividing an incident beam of coherent radiation having a wavelength effective to excite the fluorophore into a plurality of excitation beamlets using a diffraction grating and directing each excitation beamlet to an excitation/detection site on the electrophoresis gel, wherein each of the excitation beamlets are of the same wavelength as the incident beam, and
(d) detecting emission from the detection sites while the sample is migrating through the gel.

26. A method according to claim 25, wherein the incident beam of coherent radiation is supplied by a laser.

27. A method according to claim 25, wherein the fluorophore is rhodamine and the incident beam of coherent radiation is supplied by a Helium Neon laser.

28. A method according to claim 25, wherein the fluorophore is Cy5.5 and the incident beam of coherent radiation is supplied by a red laser diode.

29. A method according to claim 25, wherein the fluorophore is fluorescein and the incident beam of coherent radiation is supplied by an argon ion laser.

30. A method according to claim 25, wherein the diffraction grating divides the incident beam into from 2 to 24 beamlets.

31. An apparatus for electrophoretic separation and real-time detection of a sample labeled with a fluorophore, comprising,
(a) a housing adapted to receive an electrophoresis gel holder;
(b) means for applying an electric field to an electrophoresis gel received within the housing;
(c) a linear array of excitation sources disposed to deliver excitation energy of a frequency suitable for excitation of the fluorophore to an array of excitation/detection sites on the gel holder, and
(d) a linear array of detectors for detecting emissions from the array of excitation/detection sites, wherein the number of excitation sources, the number of excitation/detection sites in the gel holder and the number of detectors are equal.

32. An apparatus according to claim 31, wherein the detectors are photodiodes.

33. An apparatus according to claim 31, wherein the excitation sources are light emitting diodes.

34. An apparatus according to claim 32, further comprising means for sequentially directing electromagnetic radiation from the array of excitation sources to at least two spatially separated groups of excitation/detection sites within the array; and means for correlating a detected emission with the irradiated excitation/detection site such that a given emission may be linked with the excitation/detection site being irradiated.

35. A method for electrophoretic separation and detection of a sample labeled with a fluorophore, comprising the steps of:
(a) loading the samples onto a plurality of lanes of an electrophoresis gel at a plurality of loading sites;
(b) applying an electric field to the loaded gel such that the samples migrate from the loading sites to a plurality of detection sites;
(c) delivering radiation from an array of excitation sources to an array of excitation/detection sites on the gel holder, and
(d) detecting emissions from the array of excitation/detection sites using an array of detectors, wherein the number of excitation sources, the number of excitation/detection sites in the gel holder and the number of detectors are equal.

36. A method according to claim 35, wherein the fluorophore is a cyanine dye.

37. A method according to claim 36, wherein the fluorophore is selected from the group consisting of Cy5, Cy5.5, Cy7, Cy7.5 and Cy9.

38. A method according to claim 35, wherein excitation sources are light emitting diodes.

39. A method according to claim 35, wherein the sample labeled with a fluorophore is an oligonucleotide.

40. A method according to claim 35, wherein the electric field applied is from 100 to 400 V/cm.

* * * * *